(12) United States Patent
Schulhauser et al.

(10) Patent No.: US 11,145,415 B2
(45) Date of Patent: *Oct. 12, 2021

(54) SYSTEMS AND METHODS FOR POST-OPERATIVE OUTCOME MONITORING

(71) Applicant: Warsaw Orthopedic, Inc., Warsaw, IN (US)

(72) Inventors: Randal Schulhauser, Phoenix, AZ (US); Richard L. Brown, Mesa, AZ (US); Jeff R. Justis, Germantown, TN (US); Matthew M. Morrison, Cordova, TN (US); Jeff M. Cherry, Minneapolis, MN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 154 days.

This patent is subject to a terminal disclaimer.

(21) Appl. No.: 16/548,109

(22) Filed: Aug. 22, 2019

(65) Prior Publication Data
US 2019/0378605 A1     Dec. 12, 2019

Related U.S. Application Data

(63) Continuation of application No. 14/945,167, filed on Nov. 18, 2015, now Pat. No. 10,445,466.

(51) Int. Cl.
*G16H 50/30* (2018.01)
*G16H 40/63* (2018.01)
(Continued)

(52) U.S. Cl.
CPC ............. *G16H 50/30* (2018.01); *G16H 20/40* (2018.01); *G16H 30/20* (2018.01); *G16H 40/63* (2018.01); *G16H 50/20* (2018.01)

(58) Field of Classification Search
CPC ......... G16H 50/30; G16H 20/40; G16H 50/20
See application file for complete search history.

(56) References Cited

U.S. PATENT DOCUMENTS

| 4,265,237 A | 5/1981 | Schwanbom et al. |
| 7,236,822 B2 | 6/2007 | Dobak, III |

(Continued)

FOREIGN PATENT DOCUMENTS

| EP | 1587418 A1 | 10/2005 |
| GB | 2452158 A | 2/2009 |

(Continued)

OTHER PUBLICATIONS

O'Shaughnessy et al., Changes in flexion-relaxation phenomenon and lumbo-pelvic kinematics following lumbar disc replacement surgery, 2013, 10:72, http://www.jneuroengrehab.com/content/10/1/72 (Year: 2013).*

(Continued)

*Primary Examiner* — Evangeline Barr
(74) *Attorney, Agent, or Firm* — Fox Rothschild LLP

(57) ABSTRACT

A system including a range of motion module, a quality of sleep module, an overall module, and a control module. The range of motion module, subsequent to performing a procedure on a patient, determines a first range of motion score of the patient based on a signal generated by a sensor. The quality of sleep module, subsequent to performing the procedure on the patient, determines a first quality of sleep score or a first pain score based on the signal generated by the sensor. The overall module determines a combined score based on (i) the first range of motion score, and (ii) the first sleep score or the first pain score. The control module (i) determines whether an outcome of the procedure is positive based on the combined score, and (ii) stores the determined outcome and the combined score in a memory.

21 Claims, 12 Drawing Sheets

(51) Int. Cl.
  *G16H 20/40* (2018.01)
  *G16H 50/20* (2018.01)
  *G16H 30/20* (2018.01)

(56) References Cited

U.S. PATENT DOCUMENTS

| | | |
|---|---|---|
| 7,496,407 B2 | 2/2009 | Odderson |
| 7,689,292 B2 | 3/2010 | Hadzic et al. |
| 7,789,833 B2 | 9/2010 | Urbano et al. |
| 7,987,001 B2 | 7/2011 | Teichman et al. |
| 7,993,269 B2 | 8/2011 | Donofrio et al. |
| 8,068,910 B2 | 11/2011 | Gerber et al. |
| 8,126,736 B2 | 2/2012 | Anderson et al. |
| 8,255,045 B2 | 8/2012 | Gharib et al. |
| 8,374,673 B2 | 2/2013 | Adcox et al. |
| 8,498,717 B2 | 7/2013 | Lee et al. |
| 8,515,520 B2 | 8/2013 | Brunnett et al. |
| 8,568,312 B2 | 10/2013 | Cusimano Reaston et al. |
| 8,568,317 B1 | 10/2013 | Gharib et al. |
| 8,594,779 B2 | 11/2013 | Denison et al. |
| 8,670,830 B2 | 3/2014 | Carlson et al. |
| 8,680,986 B2 | 3/2014 | Costantino |
| 8,688,237 B2 | 4/2014 | Stanislaus et al. |
| 8,805,527 B2 | 8/2014 | Mumford et al. |
| 8,886,280 B2 | 11/2014 | Kartush |
| 8,892,259 B2 | 11/2014 | Bartol et al. |
| 8,926,509 B2 | 1/2015 | Magar et al. |
| 8,956,418 B2 | 2/2015 | Wasielewski et al. |
| 8,989,855 B2 | 3/2015 | Murphy et al. |
| 9,031,658 B2 | 5/2015 | Chiao et al. |
| 9,078,671 B2 | 7/2015 | Beale et al. |
| 9,084,550 B1 | 7/2015 | Bartol et al. |
| 9,084,551 B2 | 7/2015 | Brunnett et al. |
| 9,204,830 B2 | 12/2015 | Zand et al. |
| 2004/0135528 A1 | 7/2004 | Yasohara et al. |
| 2004/0215074 A1* | 10/2004 | Giuliano ............. A61B 5/055 600/415 |
| 2005/0075067 A1 | 4/2005 | Lawson et al. |
| 2005/0149143 A1 | 7/2005 | Libbus et al. |
| 2005/0159659 A1 | 7/2005 | Sawan et al. |
| 2005/0215993 A1 | 9/2005 | Phan |
| 2006/0241725 A1 | 10/2006 | Libbus et al. |
| 2006/0276702 A1 | 12/2006 | McGinnis |
| 2007/0208597 A1 | 9/2007 | Recknor et al. |
| 2007/0282217 A1 | 12/2007 | McGinnis et al. |
| 2008/0183915 A1 | 7/2008 | Iima |
| 2008/0214903 A1 | 9/2008 | Orbach |
| 2008/0218393 A1 | 9/2008 | Kuramochi et al. |
| 2008/0300650 A1 | 12/2008 | Gerber et al. |
| 2008/0306348 A1 | 12/2008 | Kuo et al. |
| 2009/0182322 A1 | 7/2009 | D'Amelio et al. |
| 2009/0240117 A1 | 9/2009 | Chmiel et al. |
| 2009/0299439 A1 | 12/2009 | Mire et al. |
| 2010/0036280 A1 | 2/2010 | Ballegaard et al. |
| 2010/0152811 A1 | 6/2010 | Flaherty |
| 2010/0152812 A1 | 6/2010 | Flaherty et al. |
| 2010/0160731 A1 | 6/2010 | Giovannini et al. |
| 2010/0168561 A1 | 7/2010 | Anderson |
| 2010/0191071 A1 | 7/2010 | Anderson et al. |
| 2010/0191311 A1 | 7/2010 | Scheiner et al. |
| 2011/0028860 A1 | 2/2011 | Chenaux et al. |
| 2011/0071418 A1 | 3/2011 | Stellar et al. |
| 2011/0160731 A1 | 6/2011 | Bleich et al. |
| 2011/0230734 A1 | 9/2011 | Fain et al. |
| 2011/0245647 A1 | 10/2011 | Stanislaus et al. |
| 2011/0270120 A1 | 11/2011 | McFarlin et al. |
| 2011/0270121 A1 | 11/2011 | Johnson et al. |
| 2012/0004516 A1 | 1/2012 | Eng et al. |
| 2012/0071784 A1 | 3/2012 | Melkent et al. |
| 2012/0130201 A1 | 5/2012 | Jain |
| 2012/0197621 A1 | 8/2012 | Jain |
| 2012/0245439 A1 | 9/2012 | Andre et al. |
| 2013/0030257 A1 | 1/2013 | Nakata et al. |
| 2013/0090641 A1 | 4/2013 | McKinney et al. |
| 2013/0185310 A1* | 7/2013 | De Guise ............. G16H 30/20 707/748 |
| 2013/0245722 A1 | 9/2013 | Ternes et al. |
| 2013/0261422 A1 | 10/2013 | Gilmore et al. |
| 2013/0274830 A1 | 10/2013 | Skelton |
| 2014/0013565 A1* | 1/2014 | MacDonald ........... G16H 20/40 29/407.05 |
| 2014/0058284 A1 | 2/2014 | Bartol et al. |
| 2014/0073985 A1 | 3/2014 | Sakai et al. |
| 2014/0074084 A1 | 3/2014 | Engeberg et al. |
| 2014/0256642 A1 | 9/2014 | Bar-Or et al. |
| 2014/0275914 A1 | 9/2014 | Li et al. |
| 2014/0276549 A1 | 9/2014 | Osorio |
| 2015/0012066 A1 | 1/2015 | Underwood |
| 2015/0088029 A1 | 3/2015 | Wybo |
| 2015/0112325 A1 | 4/2015 | Whitman |
| 2015/0202395 A1 | 7/2015 | Fromentin |
| 2015/0203592 A1 | 7/2015 | Wang |
| 2015/0238260 A1 | 8/2015 | Nau, Jr. |
| 2015/0250423 A1 | 9/2015 | Hacker et al. |
| 2016/0015299 A1 | 1/2016 | Chan et al. |
| 2016/0030281 A1 | 2/2016 | Shafieloo |
| 2016/0038072 A1 | 2/2016 | Brown et al. |
| 2016/0038073 A1 | 2/2016 | Brown et al. |
| 2016/0038074 A1 | 2/2016 | Brown et al. |
| 2016/0081594 A1 | 3/2016 | Gaddipati et al. |
| 2016/0199659 A1 | 7/2016 | Jiang et al. |
| 2016/0235999 A1 | 8/2016 | Nuta et al. |
| 2016/0262699 A1 | 9/2016 | Goldstone et al. |
| 2016/0270679 A1 | 9/2016 | Mahon et al. |
| 2016/0287112 A1 | 10/2016 | McFarlin et al. |
| 2016/0287861 A1 | 10/2016 | McFarlin et al. |
| 2016/0317053 A1 | 11/2016 | Srivastava |
| 2017/0140121 A1 | 5/2017 | Schulhauser et al. |

FOREIGN PATENT DOCUMENTS

| | | |
|---|---|---|
| WO | 99/37359 A1 | 7/1999 |
| WO | 02/082982 A1 | 10/2002 |
| WO | 2004064632 A1 | 8/2004 |
| WO | 2006/026482 A2 | 3/2006 |
| WO | 2011/150502 A2 | 12/2011 |
| WO | 2013/019757 A2 | 2/2013 |
| WO | 2013/151770 A1 | 10/2013 |
| WO | 2015069962 A1 | 5/2015 |

OTHER PUBLICATIONS

International Search Report and Written Opinion dated Nov. 29, 2017 in corresponding International Application No. PCT/US2017/051825.

International Preliminary Report on Patentability dated Oct. 12, 2017 in corresponding/related International Application No. PCT/US2016/023903.

International Search Report and Written Opinion for PCT/US2016/023910 dated Aug. 5, 2016 which claims benefit of U.S. Appl. No. 14/578,452, filed Apr. 3, 2015.

International Search Report and Written Opinion for PCT/US2016/023903 dated Sep. 19, 2016 which claims benefit of U.S. Appl. No. 14/678,485, filed Apr. 3, 2015.

International Preliminary Report on Patentability dated Oct. 12, 2017 in corresponding/related International Application No. PCT/US2016/023910.

Cypress Perform. SPI-based CyFiTM Transceiver Data Sheet. Cypress Semiconductor Corporation. (Jun. 25, 2009) pp. 1-45.

Hurley "Physiotherapy for Sleep Disturbance in Chronic Low Pack Pain: a Feasibility Randomised Controlled Trial" BMC Musculoskeletal Disorders; 11 pages; 2010.

International Search Report and Written Opinion for PCT/US2015/043844 dated Jan. 12, 2016.

Invitation to Pay Additional Fees dated Jun. 10, 2016 for International Application No. PCT/US2016/023903 which corresonds to U.S. Appl. No. 14/678,485, filed Apr. 3, 2015.

Wustrack "Change in Physical Activity One Year after Lumbar Decompression with or without Fusion, is it Correlated to Self-

(56) References Cited

OTHER PUBLICATIONS

Reported Outcome Scores?" Proceedings of NASS 20th Annual Meeting/The Spine Journal 5 (2005) IS-189S.

Wustrack "Physical Activity does not correlate with HRQL Scores in Patients with Degeneratie Lumbar Conditions" Proceedings of the NASS 20th Annual Meeting/The Spine Journal 5 (2005) IS-189S.

* cited by examiner

| Day | Surrogate RoM (Activity) | | | | | Surrogate Pain (Quality of Sleep) | | | | | Study Results | Outcome Score |
|---|---|---|---|---|---|---|---|---|---|---|---|---|
| | 0 to 2.5 | 2.6 to 5 | 5.1 to 7.5 | 7.6 to 10 | Daily Avg | 0 to 2.5 | 2.6 to 5 | 5.1 to 7.5 | 7.6 to 10 | Daily Avg | | |
| 1 | 82% | 17% | 1% | 0% | 1.725 | 0% | 0% | 15% | 85% | 1.625 | | |
| 2 | 88% | 12% | 0% | 0% | 1.550 | 5% | 5% | 5% | 85% | 2.000 | | |
| 3 | 85% | 5% | 5% | 5% | 2.000 | 1% | 3% | 6% | 90% | 1.625 | | |
| 4 | 86% | 13% | 1% | 0% | 1.625 | 10% | 10% | 18% | 67% | 3.103 | | |
| 5 | 80% | 10% | 8% | 2% | 2.050 | 12% | 13% | 25% | 50% | 3.425 | | |
| 6 | 91% | 8% | 1% | 0% | 1.500 | 15% | 20% | 35% | 30% | 4.250 | | |
| 7 | 75% | 15% | 6% | 4% | 2.225 | 17% | 25% | 30% | 28% | 4.525 | | |
| 8 | 77% | 23% | 0% | 0% | 1.825 | 20% | 30% | 40% | 10% | 5.250 | | |
| 9 | 88% | 10% | 1% | 1% | 1.625 | 20% | 28% | 37% | 15% | 5.075 | | |
| 10 | 67% | 30% | 2% | 1% | 2.175 | 15% | 15% | 35% | 25% | 4.500 | | |
| Pre-Op Score | 82% | 14% | 3% | 1% | 18.3 | 12% | 16% | 25% | 49% | 35.3 | | |
| Combined Pre-Op Score | | | | | | | | | | | 53.6 | |
| Surgery on Day 11 | | | | | | | | | | | | |
| Recovery Day 12 thru 42 | | | | | | | | | | | | |
| 43 | 80% | 17% | 1% | 2% | 1.875 | 15% | 25% | 25% | 35% | 4.250 | | |
| 44 | 78% | 22% | 0% | 0% | 1.800 | 17% | 28% | 25% | 30% | 4.550 | | |
| 45 | 75% | 15% | 5% | 5% | 2.250 | 20% | 30% | 30% | 20% | 5.000 | | |
| 46 | 75% | 18% | 7% | 5% | 2.488 | 22% | 33% | 28% | 17% | 5.250 | | |
| 47 | 70% | 20% | 8% | 2% | 2.300 | 25% | 35% | 25% | 15% | 5.500 | | |
| 48 | 67% | 23% | 10% | 0% | 2.325 | 30% | 35% | 20% | 15% | 5.750 | | |
| 49 | 65% | 25% | 8% | 2% | 2.425 | 33% | 37% | 20% | 10% | 6.075 | | |
| 50 | 63% | 17% | 15% | 5% | 2.800 | 35% | 30% | 25% | 10% | 6.000 | | |
| 51 | 60% | 20% | 15% | 5% | 2.875 | 38% | 42% | 15% | 5% | 6.575 | | |
| 52 | 55% | 23% | 21% | 1% | 2.950 | 40% | 40% | 20% | 0% | 6.750 | | |
| Post-Op Score | 69% | 20% | 9% | 3% | 24.1 | 28% | 34% | 23% | 16% | 55.7 | | |
| Combined Post-Op Score | | | | | | | | | | | 79.8 | |
| Outcome Score | | | | | | | | | | | | 26.2 |

FIG. 11

SYSTEMS AND METHODS FOR POST-OPERATIVE OUTCOME MONITORING

CROSS-REFERENCE TO RELATED APPLICATIONS

This application claims benefit to U.S. application Ser. No. 14/945,167, filed on Nov. 18, 2015, and entitled "SYSTEMS AND METHODS FOR POST-OPERATIVE MONITORING". Moreover, the present disclosure relates to U.S. application Ser. No. 14/945,208, filed on Nov. 18, 2015, and entitled "SYSTEMS AND METHODS FOR PRE-OPERATIVE PROCEDURE DETERMINATION AND OUTCOME PREDICTING", now U.S. Pat. No. 10,339,273. The disclosures of the above applications are incorporated herein by reference in their entirety.

FIELD

The present disclosure relates to patient sensor monitoring systems and devices.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

A subject, such as a human patient, may select or be required to undergo a surgical procedure to correct or augment an anatomy of the patient. The augmentation of the anatomy can include various procedures, such as movement or augmentation of bone, insertion of implantable devices, or other appropriate procedures. A surgeon can perform the procedure on the patient based on images of the patient, which can be acquired using an x-ray scanner having an imaging system. The images may be acquired prior to or during the procedure. The imaging system may be, for example, an O-Arm® or C-arm imaging system or a kinematics imaging system. The images may be fluoroscopic or radiographic images depending on an operating mode of the imaging system.

The acquired images of the patient can assist a surgeon in planning and performing the procedure. A surgeon may select a two dimensional image or a three dimensional image representation of the patient. The images can assist the surgeon in performing a procedure with a less invasive technique by allowing the surgeon to view the anatomy of the patient without removing overlying tissue (including dermal and muscular tissue) when performing a procedure. An O-Arm imaging system includes an 'O'-shaped gantry and a 'O'-shaped rotor. A C-Arm imaging system includes a 'C'-shaped gantry and a 'C'-shaped rotor. Each of these imaging systems typically includes an x-ray source and an x-ray detector mounted opposite each other on the corresponding rotor. Each of the x-ray sources generates x-rays, which are directed at a subject. Each of the x-ray detectors detects the x-rays subsequent to the x-rays passing through the subject.

Prior to performing a procedure, a surgeon must determine whether a procedure is needed and estimate a probability that the procedure will be successful. Currently, spinal surgeons generally determine the need for surgery in a subjective manner after a physical examination and a review of x-ray images of a patient. Arbitrary "cut-points" can be determined based on surgical experience of the surgeon.

SUMMARY

A system is provided and includes a range of motion module, a quality of sleep module, an overall module, and a control module. The range of motion module is configured to, subsequent to performing a procedure on a patient, determine a first range of motion score of the patient based on a signal generated by a sensor. The quality of sleep module is configured to, subsequent to performing the procedure on the patient, determine a first quality of sleep score or a first pain score based on the signal generated by the sensor. The overall module is configured to determine a combined score based on (i) the first range of motion score, and (ii) the first sleep score or the first pain score. The control module is configured to (i) determine whether an outcome of the procedure is positive based on the combined score, and (ii) store the determined outcome and the combined score in a memory.

In other features, a method is provided and includes: subsequent to performing a procedure on a patient, determining a first range of motion score of the patient based on a signal generated by a sensor; subsequent to performing the procedure on the patient, determining a first quality of sleep score or a first pain score based on the signal generated by the sensor; determining a combined score based on (i) the first range of motion score, and (ii) the first sleep score or the first pain score; determining whether an outcome of the procedure is positive based on the combined score; and storing the determined outcome and the combined score in a memory.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF DRAWINGS

FIG. 11 is a table of pre-operation and post-operation range of motion and pain scores in accordance with the present disclosure.

In the drawings, reference numbers may be reused to identify similar and/or identical elements.

DESCRIPTION

The following disclosed examples include pre-operative and post-operative monitoring of relevant physiologic parameters. The parameters are analyzed to determine "cut-points" and whether performance of a procedure is likely to provide a positive outcome. This provides a surgeon with an objective method to determine whether a spinal procedure is likely to provide a positive outcome.

A current standard of care for spinal fusion and other spinal surgical procedures does not include pre-operative variable data techniques to determine both (i) whether a procedure should be performed, and (ii) if the procedure is performed, whether the procedure has an acceptable probability to achieve a positive outcome. The following disclosed examples provide objective thresholds (or objective "cut-points") for determining whether to perform a procedure based on a probability of a positive outcome. The examples include pre-operative and post-operative monitoring of various parameters and may include determining sensor-based and/or image-based "cut-points" for determining a need for surgery. The following examples include pre-operative data collection and monitoring of physiological parameters, which may be combined with pre-operative imaging techniques, to achieve predictive positive outcomes.

Figure 1:
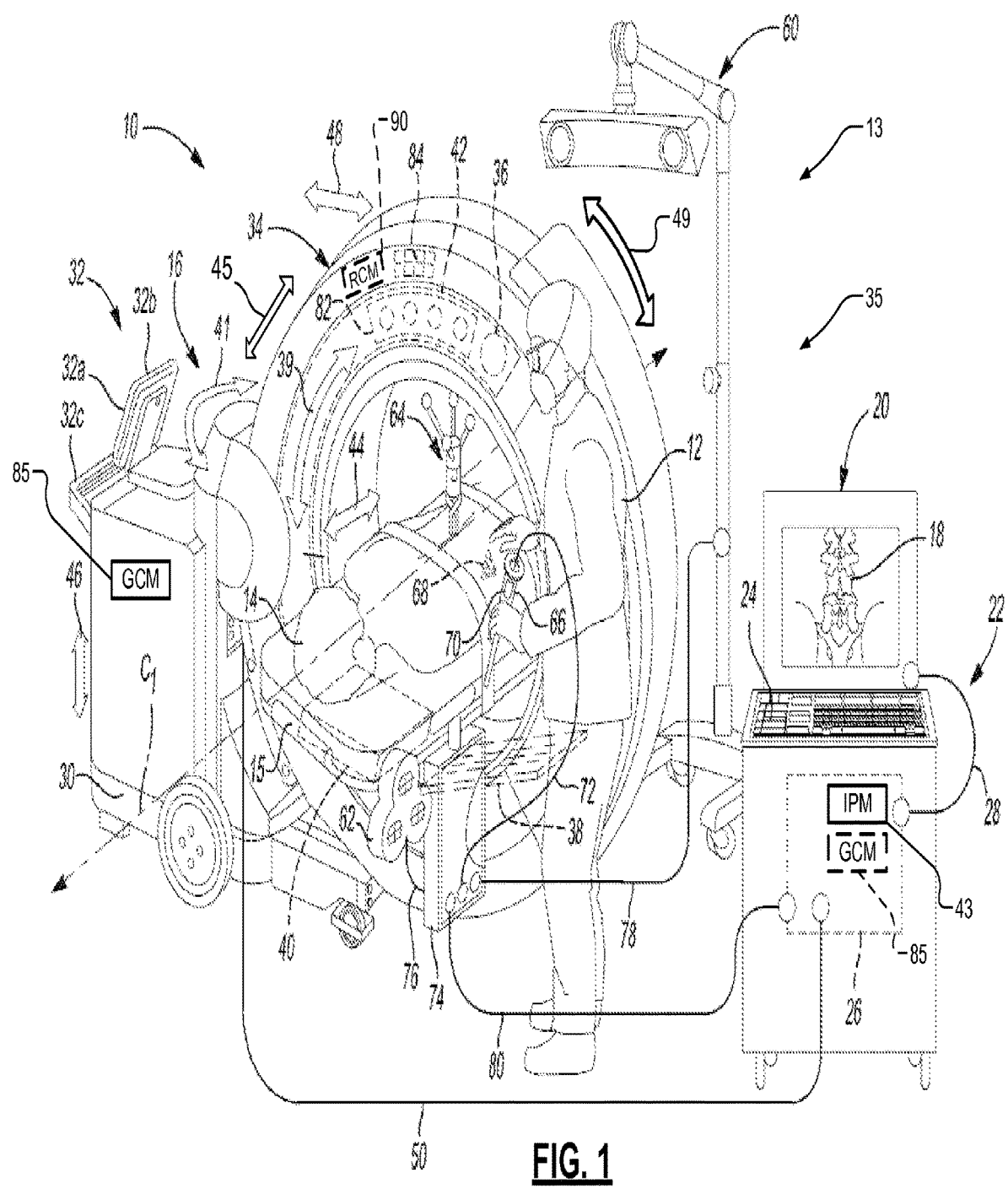
FIG. 1 is an environmental view of an imaging system in an operating theatre, including gantry positioning system in accordance with an embodiment of the present disclosure.

FIG. 1 shows an operating theatre (or inside of an operating room) 10 and a user 12 (e.g., a physician) performing a procedure on a subject (e.g., a patient) 14. In performing the procedure, the user 12 uses a procedural operating system 13 that includes an imaging system 16 to acquire image data of the patient 14. The image data acquired of the patient 14 can include two-dimension (2D) or three-dimensional (3D) images. Models may be generated using the acquired image data. The model can be a three-dimension (3D) volumetric model generated based on the acquired image data using various techniques, including algebraic iterative techniques. The image data (designated 18) can be displayed on a display device 20, and additionally, may be displayed on a display device 32a associated with an imaging computing system 32. The displayed image data 18 may include 2D images, 3D images, and/or a time changing 4D images. The displayed image data 18 may also include acquired image data, generated image data, and/or a combination of the acquired and generated image data.

Image data acquired of a patient 14 may be acquired as 2D projections. The 2D projections may then be used to reconstruct 3D volumetric image data of the patient 14. Also, theoretical or forward 2D projections may be generated from the 3D volumetric image data. Accordingly, image data may be used to provide 2D projections and/or 3D volumetric models.

The display device 20 may be part of a computing system 22. The computing system 22 may include a variety of computer-readable media. The computer-readable media may be any available media that is accessed by the computing system 22 and may include both volatile and non-volatile media, and removable and non-removable media. By way of example, the computer-readable media may include computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the computing system 22. The computer-readable media may be accessed directly or through a network such as the Internet.

In one example, the computing system 22 can include an input device 24, such as a keyboard, and one or more processors 26 (the one or more processors may include multiple-processing core processors, microprocessors, etc.) that may be incorporated with the computing system 22. The input device 24 may include any suitable device to enable a user to interface with the computing system 22, such as a touchpad, touch pen, touch screen, keyboard, mouse, joy-stick (sometimes referred to as a joystick controller), trackball, wireless mouse, audible control or a combination thereof. Furthermore, while the computing system 22 is described and illustrated herein as comprising the input device 24 discrete from the display device 20, the computing system 22 may include a touchpad or tablet computing device and may be integrated within or be part of the imaging computing system 32. A connection (or communication line) 28 may be provided between the computing system 22 and the display device 20 for data communication to allow driving the display device 20 to illustrate the image data 18.

The imaging system 16 may be an O-Arm® imaging system, a C-Arm imaging system or other suitable imaging system. The imaging system 16 may include a mobile cart 30, the imaging computing system 32 and a gantry 34 (or x-ray scanner gantry). The gantry 34 includes an x-ray source 36, a collimator (not shown), a multi-row detector 38, a flat panel detector 40 and a rotor 42. The mobile cart 30 may be moved from one operating theater or room to another and the gantry 34 may be moved relative to the mobile cart 30. This allows the imaging system 16 to be mobile and used for various procedures without requiring a capital expenditure or space dedicated to a fixed imaging system. Although the gantry 34 is shown as being mobile, the gantry 34 may not be connected to the mobile cart 30.

The imaging system 16, the mobile cart 30 and/or the imaging computing system 32 may include motors, positioning devices, coupling members, circuit elements, controllers (or control modules), sensors, etc. (examples of which are shown in and described with respect to FIGS. 3-6) for moving and orienting the gantry 34 relative to the table 15 and/or the patient 14. The motors, positioning devices, coupling members, circuit elements, controllers (or control modules), sensors, etc. are part of a gantry positioning system 35.

The gantry 34 may define an isocenter of the imaging system 16. In this regard, a centerline C1 through the gantry 34 defines an isocenter or center of the imaging system 16. Generally, the patient 14 can be positioned along the centerline C1 of the gantry 34, such that a longitudinal axis of the patient 14 is aligned with the isocenter of the imaging system 16.

The imaging computing system 32 may control the movement, positioning and adjustment of the multi-row detector 38, the flat panel detector 40 and the rotor 42 independently to enable image data acquisition via an image processing module 43 of the processor 26. The processed images may be displayed on the display device 20.

During operation, the source 36 emits x-rays through the patient 14, which are detected by the multi-row detector 38 or the flat panel detector 40. The x-rays emitted by the source 36 may be shaped by the collimator and emitted for detection by the multi-row detector 38 or the flat panel detector 40. The collimator may include one or more leaves, which may be controlled to shape the x-rays emitted by the source 36. The collimator may shape the x-rays emitted by the source 36 into a beam that corresponds with the shape of the multi-row detector 38 and the flat panel detector 40. The multi-row detector 38 may be selected to acquire image data of low contrast regions of the anatomy, such as regions of soft tissue. The flat panel detector 40 may be selected to acquire image data of high contrast regions of the anatomy, such as bone. The source 36, the collimator, the multi-row detector 38 and the flat panel detector 40 may each be coupled to and/or mounted on the rotor 42.

The multi-row detector 38 and the flat panel detector 40 may be coupled to the rotor 42 to be (i) diametrically opposed from the source 36 and the collimator within the gantry 34, and (ii) independently movable relative to each other and into alignment with the source 36 and the collimator. In one example, the multi-row detector 38 may be positioned such that the flat panel detector 40 may be adjacent to the multi-row detector 38. In one alternative example, the flat panel detector 40 may be moved over the multi-row detector 38 into alignment with the source 36 when an image using the flat panel detector 40 is acquired. In another example, the multi-row detector 38 may be positioned over the flat panel detector 40. As a further alternative, the multi-row detector 38 and the flat panel detector 40 may each be separately movable, such that the selected multi-row detector 38 or flat panel detector 40 may be aligned with the source 36 and the collimator. The selected one of the multi-row detector 38 and the flat panel detector 40 may be aligned with the source 36 and the collimator when the selected one of the multi-row detector 38 and the flat panel detector 40 is substantially opposite or about 180 degrees apart from the source 36 and the collimator.

As the source 36, collimator, multi-row detector 38 and flat panel detector 40 are coupled to the rotor 42, the source 36, collimator, multi-row detector 38 and flat panel detector 40 are movable within the gantry 34 about the patient 14. Thus, the multi-row detector 38 and the flat panel detector 40 are able to be rotated in a 360° motion around the patient 14, as indicated by arrow 39. The source 36 and collimator may move in concert with at least one of the multi-row detector 38 and the flat panel detector 40 such that the source 36 and collimator remain generally 180° apart from and opposed to the multi-row detector 38 or flat panel detector 40.

The gantry 34 has multiple degrees of freedom of motion. The gantry 34 may be isometrically swayed or swung (herein also referred to as iso-sway) relative to table 15 on which the patient 14 is disposed. The isometric swing (sometimes referred to as a wag (or yaw) angle or wag axis) is indicated by arrow 41. The gantry 34 may be: tilted relative to the patient 14 as indicated by arrow 45 (sometimes referred to as the tilt (or roll) angle or tilt axis); moved longitudinally relative to the patient 14 as indicated by arrow 44 (sometimes referred to as the z-axis); moved up and down relative to the mobile cart 30 and transversely to the patient 14 as indicated by arrow 46 (sometimes referred to as the y-axis); moved away from or towards the mobile cart 30 as indicated by arrow 48 (sometimes referred to as the x-axis); and rotated about a point on the mobile cart 30 as indicated by arrow 49 (sometimes referred to as a pitch angle or pitch axis). The degrees of freedom of motion may be represented using the Cartesian coordinate system. These degrees of freedom of motion are provided by the gantry positioning system 35 and allow a user to move the gantry relative to the table 15 and the patient 14 with minimal effort by the user. These different degrees of freedom of motion of the gantry 34 allow the source 36, collimator, multi-row detector 38 and flat panel detector 40 to be positioned relative to the patient 14.

The imaging system 16 may be precisely controlled by the imaging computing system 32 to move the source 36, collimator, the multi-row detector 38 and the flat panel detector 40 relative to the patient 14 to generate precise image data of the patient 14. In addition, the imaging system 16 may be connected with the processor 26 via connection 50 which includes a wired or wireless connection or physical media transfer from the imaging system 16 to the processor 26. Thus, image data collected with the imaging system 16 may also be transferred from the imaging computing system 32 to the computing system 22 for navigation, display, reconstruction, etc.

The imaging system 16 may also be used during an unnavigated or navigated procedure. In a navigated procedure, a localizer, including either or both of an optical localizer 60 and an electromagnetic localizer 62, may be used to generate a field or receive or send a signal within a navigation domain relative to the patient 14. If desired, the components of a navigation system associated with performing a navigated procedure may be integrated within the imaging system 16. The navigated space or navigational domain relative to the patient 14 may be registered to the image data 18 to allow registration of a navigation space defined within the navigational domain and an image space defined by the image data 18. A patient tracker (or a dynamic reference frame) 64 may be connected to the patient 14 to allow for a dynamic registration and maintenance of the registration of the patient 14 to the image data 18.

An instrument 66 may then be tracked relative to the patient 14 to allow for a navigated procedure. The instrument 66 may include an optical tracking device 68 and/or an electromagnetic tracking device 70 to allow for tracking of the instrument 66 with either or both of the optical localizer 60 or the electromagnetic localizer 62. The instrument 66 may include a communication line 72 with a navigation interface device 74, which may communicate with the electromagnetic localizer 62 and/or the optical localizer 60. The navigation interface device 74 may then communicate with the processor 26 via a communication line 80. The connections or communication lines 28, 50, 76, 78, or 80 can be wire based as shown or the corresponding devices may communicate wirelessly with each other. The imaging system 16 having the integrated navigation system tracks the instrument 66 relative to the patient 14 to allow for illustration of the tracked location of the instrument 66 relative to the image data 18 for performing a procedure.

The instrument 66 may be an interventional instrument and/or an implant. Implants may include a ventricular or vascular stent, a spinal implant, neurological stent or the like. The instrument 66 may be an interventional instrument such as a deep brain or neurological stimulator, an ablation device, or other appropriate instrument. Tracking the instrument 66 allows for viewing the location of the instrument 66 relative to the patient 14 with use of the registered image data 18 and without direct viewing of the instrument 66 within the patient 14. For example, the instrument 66 may be graphically illustrated as an icon superimposed on the image data 18.

Further, the imaging system 16 may include a tracking device, such as an optical tracking device 82 or an electromagnetic tracking device 84 to be tracked with a respective optical localizer 60 or the electromagnetic localizer 62. The tracking devices 82, 84 may be associated directly with the source 36, multi-row detector 38, flat panel detector 40, rotor 42, the gantry 34, or other appropriate part of the imaging system 16 to determine the location or position of the source 36, multi-row detector 38, flat panel detector 40, rotor 42 and/or gantry 34 relative to a selected reference frame. As illustrated, the tracking devices 82, 84 may be positioned on the exterior of the housing of the gantry 34. Accordingly, portions of the imaging system 16 including the instrument 66 may be tracked relative to the patient 14 to allow for initial registration, automatic registration or continued registration of the patient 14 relative to the image data 18.

The image processing module 43 may receive user input data from the input device 32c and may output the image data 18 to the display device 20 or the display device 32a. The user input data may include a request to acquire image data of the patient 14. Based on the user input data, the image processing module 43 may generate a detector signal and a motion signal. The detector signal may include a selected detector for image acquisition. The motion signal may include a motion profile for the rotor 42 to move to a selected location to acquire image data. The motion signal may be a command or instruction signal that is provided from the image processing module to a gantry control module 85. The gantry control module 85 may be included in the imaging computing system 32, on the mobile cart 30, or as part of the processor 26. The image processing module 43 may also send a source signal to the source 36. The source signal may command the source 36 to output or emit at least one or more x-ray pulses. The image processing module 43 may also send a collimator signal to the collimator. The collimator signal may indicate a selected shape of one or more collimated x-ray pulses. The selected shape of the collimated x-ray pulses may correspond to the selected one of the multi-row detector 38 and the flat panel detector 40. In this regard, if the multi-row detector 38 is selected, the collimated x-ray pulses may be shaped by the collimator to match the shape of the multi-row detector 38. If the flat panel detector 40 is selected, then the collimated x-ray pulses may be shaped by the collimator to match the shape of the flat panel detector 40.

The image processing module 43 may also receive as input a multi-row detector signal, which may include the one or more collimated x-ray pulses detected by the multi-row detector 38. The image processing module 43 may receive as input a flat panel detector signal, which may include the one or more collimated x-ray pulses detected by the flat panel detector 40. Based on the received collimated x-ray pulses, the image processing module 43 may generate the image data 18.

In one example, the image data 18 may include a single 2D image. In another example, the image processing module 43 may perform automatic reconstruction of an initial 3D model of an area of interest of the patient 14. Reconstruction of the 3D model may be performed in any appropriate manner, such as using algebraic techniques for optimization. The algebraic techniques may include Expectation maximization (EM), Ordered Subsets EM (OS-EM), Simultaneous Algebraic Reconstruction Technique (SART) and total variation minimization. A 3D volumetric reconstruction may be provided based on the 2D projections.

The algebraic techniques may include an iterative process to perform a reconstruction of the patient 14 for display as the image data 18. For example, a pure or theoretical image data projection, based on or generated from an atlas or stylized model of a "theoretical" patient, may be iteratively changed until the theoretical projection images match the acquired 2D projection image data of the patient 14. Then, the stylized model may be appropriately altered as the 3D volumetric reconstruction model of the acquired 2D projection image data of the patient 14 and may be used in a surgical intervention, such as navigation, diagnosis, or planning interventions. In this regard, the stylized model may provide additional detail regarding the anatomy of the patient 14, which may enable the user 12 to plan the surgical intervention efficiently. The theoretical model may be associated with theoretical image data to construct the theoretical model. In this way, the model or the image data 18 may be built based upon image data acquired of the patient 14 with the imaging system 16. The image processing module 43 may output the image data 18 to the display device 32a.

The gantry control module 85 may receive as an input detector signal and the motion signal from the image processing module 43. The gantry control module 85, based on the detector signal and the motion signal may transmit (via wires or wirelessly) control signals to a rotor control module 90. The rotor control module 90 may be located on the rotor 42. Based on the detector signal, the gantry control module 85 may generate a first move signal to move the selected one of the multi-row detector 38 or the flat panel detector 40 into alignment with the source 36 and the collimator. Based on the motion signal, the gantry control module 85 may also generate a second move signal for the rotor 42 to move or rotate the rotor 42 within the gantry 34 relative to the patient 14. A third move signal may be generated based on the motion signal and provided to the rotor control module 90. The rotor 42 may be rotated to move the source 36, the collimator, the multi-row detector 38 and the flat panel detector 40 360° around the longitudinal axis of the patient 14 within the gantry 34. The rotor may be continuously rotated in a single direction more than 360°. The movement of the source 36, the collimator, the multi-row detector 38 and the flat panel detector 40 about the patient 14 may be controlled to acquire image data at selected locations and orientations relative to the patient 14.

The 2D image data may be acquired at each of multiple annular positions of the rotor 42. The 3D image data may be generated based on the 2D image data. Also, the gantry 34, the source 36, the multi-row detector 38 and the flat panel detector 40 may not be moved in a circle, but rather may be moved in another pattern, such as a spiral helix, or other rotary movement about or relative to the patient 14. This can reduce exposure of a patient to radiation. The pattern (or path) may be non-symmetrical and/or non-linear based on movements of the imaging system 16, such as the gantry 34. In other words, the path may not be continuous in that the gantry 34 may be stopped and moved back in a direction along the path the gantry 34 previously followed. This may include following previous oscillations of the gantry 34.

The sensors, modules, processors and/or controllers of the systems 16, 22, 32 may communicate with each other and share data, signals and/or information disclosed herein. Inputs to the imaging system 16 may be received at the input device 32c, input device 24, or other control modules (not shown) within the computing system 22 or imaging computing system 32, and/or determined by other sub-modules (not shown) within the image processing module 43. The image processing module 43 may receive user input data requesting that image data of the patient 14 be acquired. The input data may include information as to whether the region of interest on the patient 14 is a high contrast region (e.g. boney tissue) or a low contrast region (e.g. soft tissue). In one example, the user input data may include a region of interest on the anatomy of the patient 14. The image processing module 43 may automatically determine to use the multi-row detector 38 or the flat panel detector 40 based on the region of interest. For example, the user may select (i) the multi-row detector 38 to acquire an image of soft tissue, and (ii) the flat panel detector 40 to acquire an image of boney tissue.

Based on the user input data, the image processing module 43 may generate source data and detector type data. The image processing module 43 may also generate motion profile data and collimator data. The source data may include information to output x-ray pulses or a signal to power-down the imaging system 16. The detector type data may include the selected multi-row detector 38 or flat panel detector 40 to acquire the image data. The motion profile data may include a selected profile for the movement of the rotor 42 within the gantry 34. The collimator data may include information to shape the x-ray pulses into collimated x-ray pulses to match the selected one of the multi-row detector 38 and flat panel detector 40.

The image processing module 43 may also receive as an input multi-row detector data and flat panel detector data. The multi-row detector data may indicate the energy from the collimated x-ray pulses received by the multi-row detector 38. The flat panel detector data may indicate the energy from the collimated x-ray pulses received by the flat panel detector 40. Based on the multi-row detector data and the flat panel detector data, the image processing module 43 may generate the image data 18 and may output this image data 18 to the display device 32a or display device 20.

The gantry control module 85 may receive as input the detector type data and the motion profile data. Based on the detector type data, the gantry control module 85 may generate flat panel move data or multi-row move data (and/or corresponding signals). The flat panel move data may include a selected position for the flat panel detector 40 to move to in order to be aligned with the source 36 and collimator. The multi-row move data may include a selected position for the multi-row detector 38 to move in order to be aligned with the source 36 and collimator.

The processor 26 or a module thereof, based on the source data, may cause the source 36 to generate pulse data for control of the collimator. The pulse data may include pulse data for at least one x-ray pulse. The processor 26 and/or a module thereof may receive as an input the multi-row move data and the collimated pulse data. Based on the multi-row move data, the multi-row detector 38 may move into alignment with the source 36. Based on the received pulse data, the processor 26 and/or a module thereof may generate the multi-row detector data (and/or a corresponding signal) for the image processing module 43. The processor 26 and/or a module thereof may receive as an input the flat panel move data and the collimated pulse data. Based on the flat panel move data, the flat panel detector 40 may move into alignment with the source 36. Based on the received pulse data, the flat panel control module may generate the flat panel detector data (and/or a corresponding signal) for the image processing module 43.

Based on the motion profile data, the gantry control module 85 may generate rotor move data (and/or a corresponding signal) for the rotor control module 90. The rotor move data may indicate a selected movement profile for the rotor 42 to move within the gantry 34 to enable the acquisition of the image data. The rotor control module 90 may receive as an input the rotor move data. Based on the rotor move data, the rotor 42 may be moved within the gantry 34 to a desired location in order to acquire the image data.

Figure 2A:
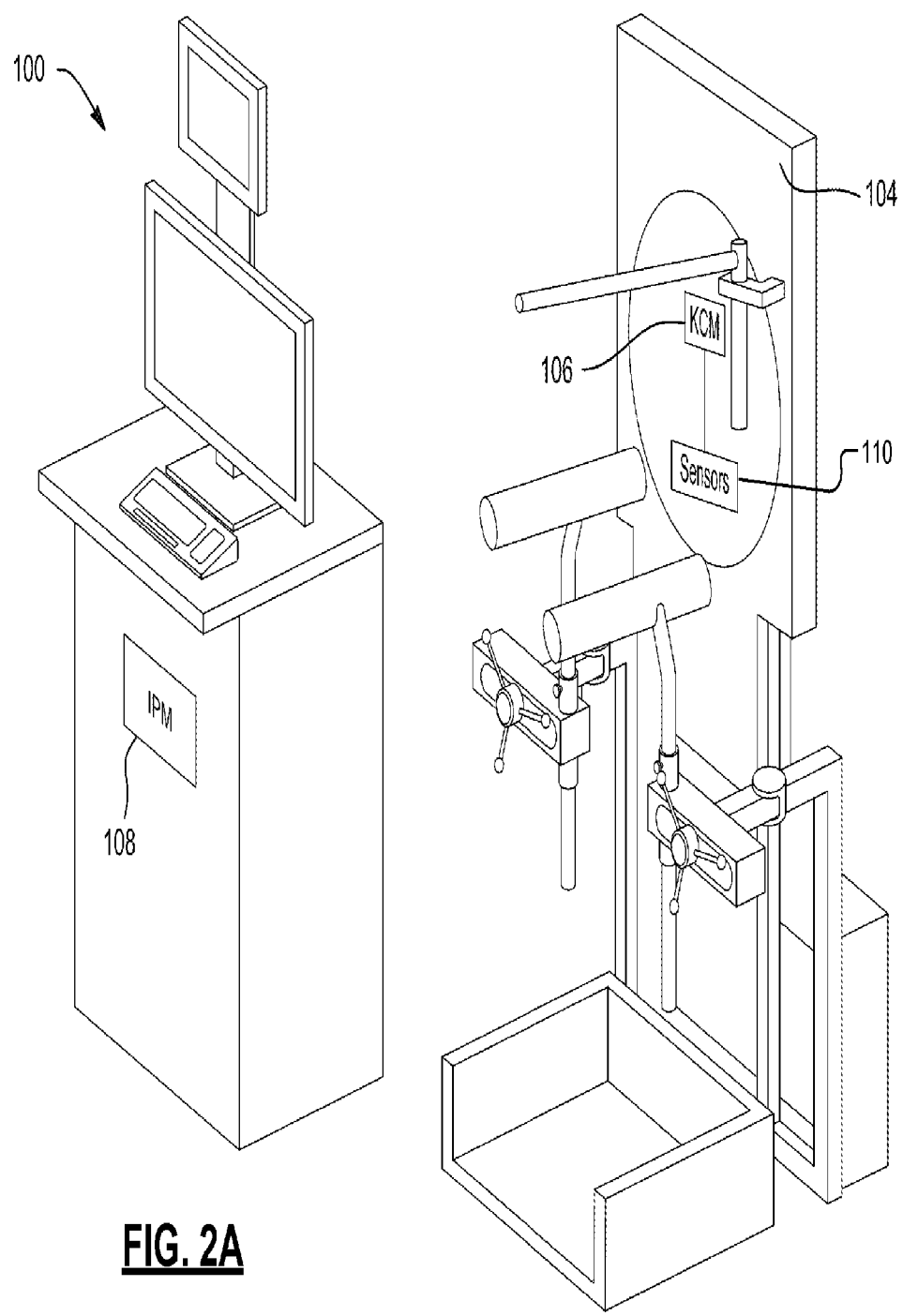
FIG. 2A is an environmental view of a spinal kinematics system including a positioning system in accordance with an embodiment of the present disclosure.
Figure 2B:
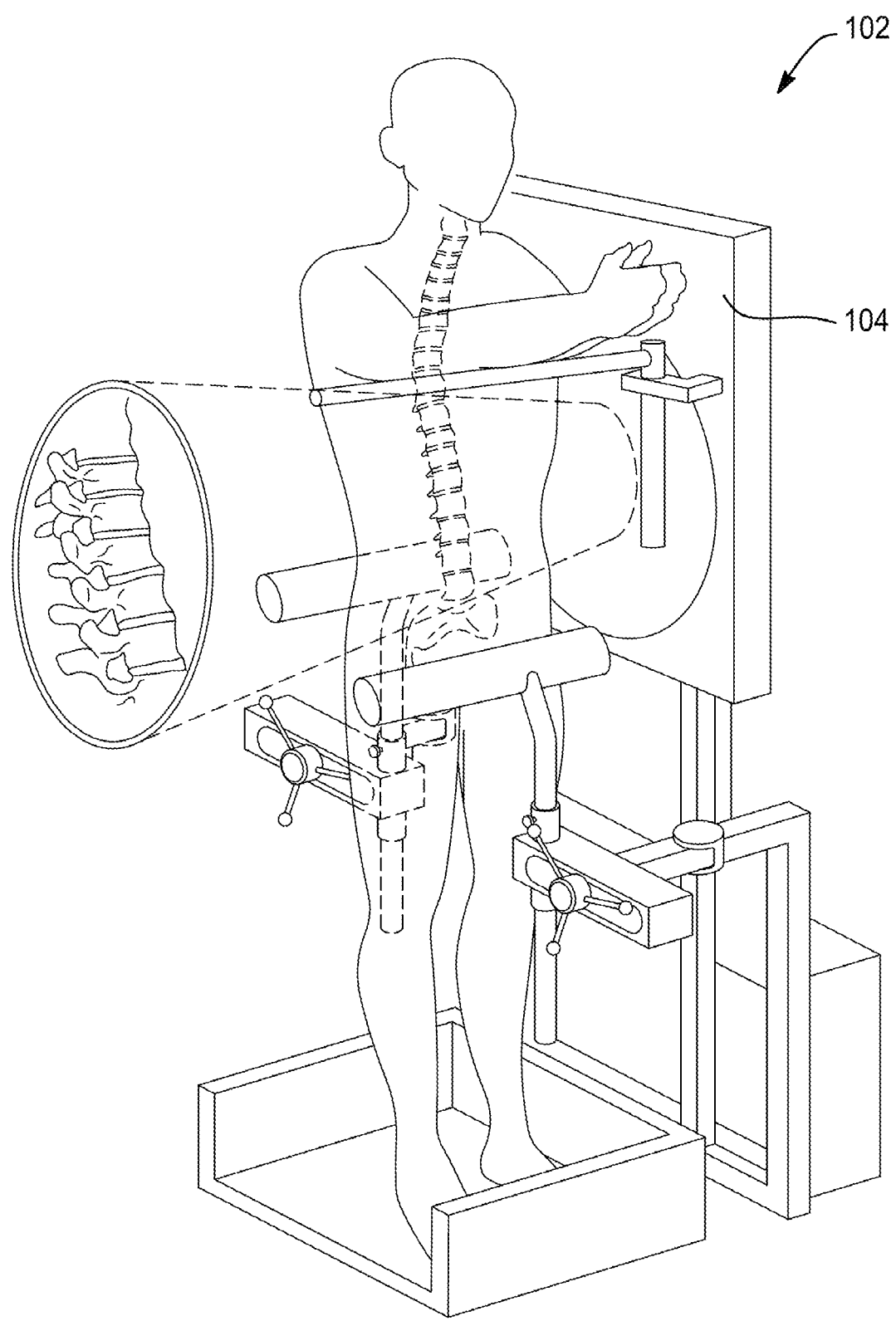
FIG. 2B is a perspective view of the positioning system of FIG. 2A illustrating x-ray imaging.

FIGS. 2A and 2B show a spinal kinematics system 100 that performs vertebral motion analysis. The spinal kinematics system 100 includes a positioning system 102, an x-ray system 104, a kinematics control module (KCM) 106, and an image processing module (IPM) 108. Unlike traditional x-rays taken to show bending of a spine in which a patient is free to bend as much as the patient desires, the positioning system 102 assists the patient through a complete spine bend. This helps to gently overcome "guarding" that often occurs during painful spine bending, which helps to assure instability (or vertebra slippage) does not go undetected.

The positioning system 102 may include sensors 110 for detecting angular positions of a patient and/or positions of vertebrae of the patient, as a patient bends his/her spine in forward and rearward directions. The x-rays system 104 takes x-ray images during bending motion of the patient to capture images of the spine of the patient. The KCM 106 may receive signals from the sensors 110, control the x-ray imaging system 104, and provide the detected signals, related position information, and/or x-ray images to the IPM 108.

Figure 3:
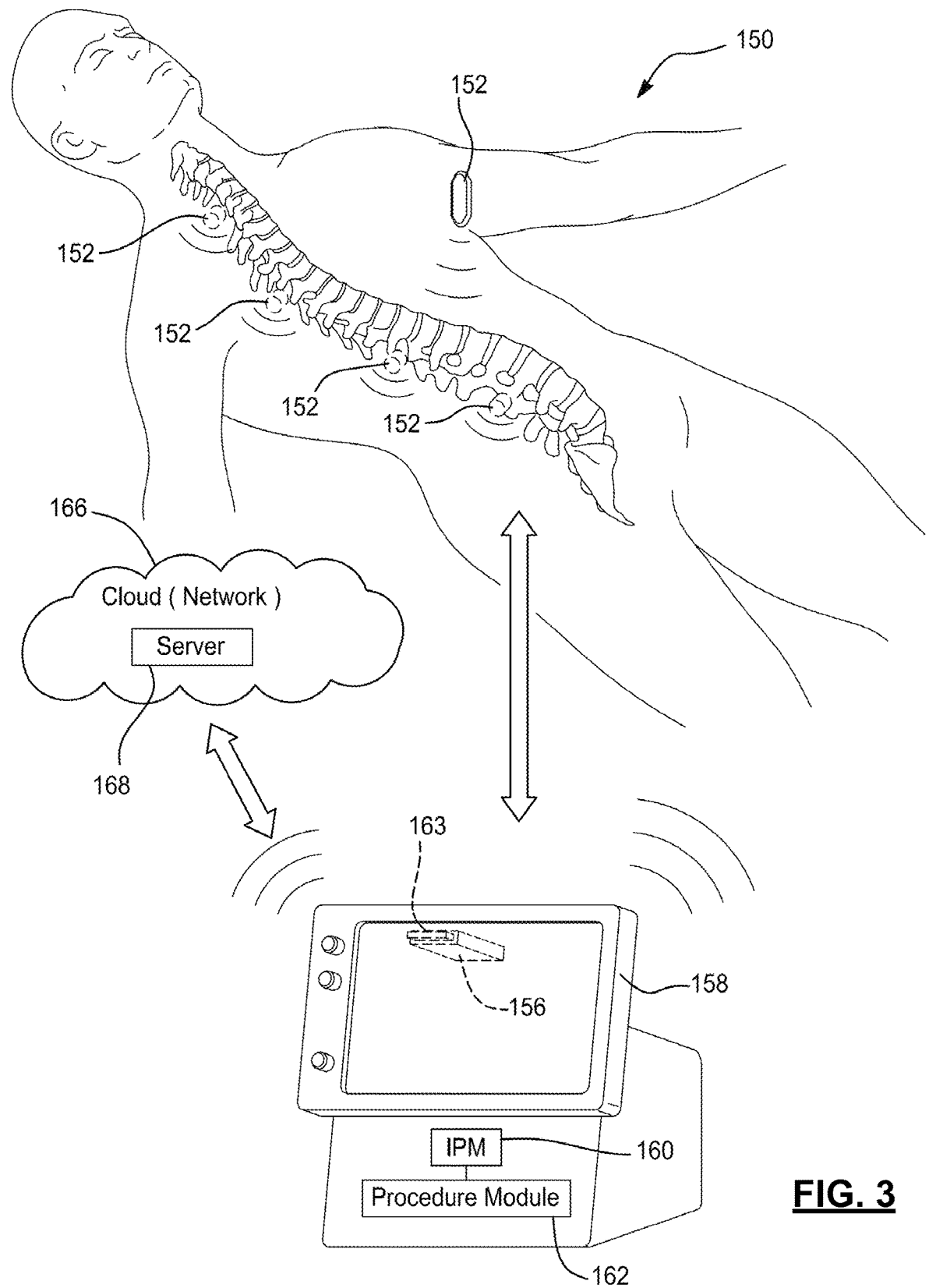
FIG. 3 is a perspective view of a wireless monitoring system incorporating sensors in accordance with the present disclosure.

FIG. 3 shows a wireless monitoring system 150. The wireless monitoring system 150, as shown, includes sensors 152, a wireless interface adaptor (WIA) 156 and a monitoring device 158. The monitoring device 158 may include an IPM 160. The IPM 160 may be implemented as and/or be in communication with one or more of the IPMs 43, 108 of FIGS. 1-2. The monitoring device 158 may be included in the systems of FIGS. 1-2. The IPM 160 may include or be in communication with a procedure module 162, which may: perform pre-operative and post-operative monitoring of parameters of a current patient and other patients; based on the parameters and previously stored outcomes of a procedure on the other patients, objectively determine whether the procedure should be performed and/or needs to be performed on the current patient; based on the parameters and corresponding outcomes of the procedure as previously performed, determine "cut-points" (or thresholds) for determining whether to perform the procedure; and based on the parameters and the determined "cut-points", predict an outcome of the procedure.

Figure 4:
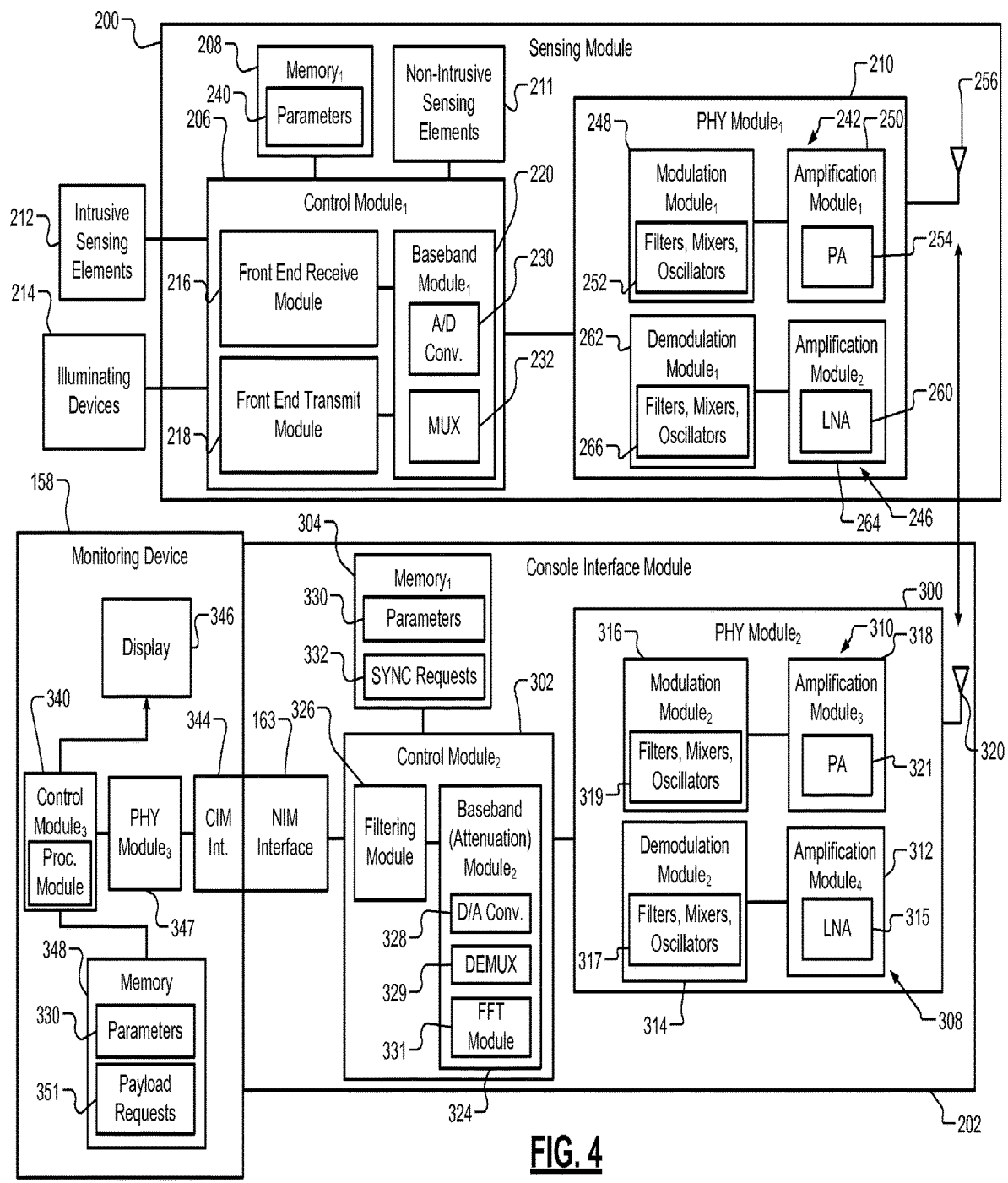
FIG. 4 is a functional block diagram of a sensing module, a console interface module and a monitoring device in accordance with the present disclosure.

The WIA 156 includes a console interface module (CIM), which is shown in FIG. 4, and an interface 163 (e.g., a 32-pin connector) for connecting to the monitoring device 158. The WIA 156 is shown as being plugged into a back side of the monitoring device 158. Although the WIA 156 is shown as being plugged into the monitoring device 158 via the interface 163, the WIA 156 may be separate from the monitoring device 158 and wirelessly communicate with the monitoring device 158. The sensors 152 wirelessly communicate with the CIM and/or the monitoring device 158. In one embodiment, the WIA 156 is connected to the monitoring device 158 and wirelessly communicates with the sensors 152. In an alternative embodiment, the monitoring device 158 includes the CIM and/or is in direct wireless communication with the sensors 152. Information described below as being transmitted from the monitoring device 158 to the CIM may then be relayed from the CIM to the sensors 152. Information and/or data described below as being transmitted from the sensors 152 to the CIM may then be relayed from the CIM to the monitoring device 158.

The WIA 156: transfers signals between (i) the monitoring device 158 and (ii) the sensors 152; and/or adds additional information to the signals received from the monitoring device 158 prior to forwarding the signals to the sensors 152, as described below. The WIA 156 may: operate essentially as a pass through device; be a smart device and add and/or replace information provided in received signals; and/or generate signals including determined information based on received signals. For example, the WIA 156 may receive a payload request signal from the monitoring device 158 and determine a delay time between when the payload request was received and when a next synchronization (SYNC) request signal is to be transmitted. The WIA 156 allows the monitoring device 158 to be compatible with legacy hardware. The WIA 156 may be unplugged from the monitoring device 158 and a traditional electrode connection box may be connected to the WIA 156 using the same interface of the monitoring device 158 as the WIA 156. The WIA 156 may replace cables connected between (i) the monitoring device 158 and (ii) the sensors 152. This eliminates wires traversing (extending from within to outside) a sterile field in which a patient is located.

As another example, the WIA 156 may receive signals from the sensors 152. The signals from the sensors 152 may indicate first parameters. The WIA 156 and/or the procedure module 162 may determine second parameters based on the received signals. The first parameters may include, for example, voltages, frequencies, current levels, durations, amplitudes, temperatures, impedances, resistances, wavelengths, etc. The second parameters may include, for example, durations, oxygen levels, temperatures, impedances, pH levels, accelerations, amplitudes, heart rates, blood pressures, electro-cardiogram (ECG) parameters, respiratory parameters, body activity values, heart sounds, blood gas pH, red blood cell counts, white blood cell counts, electro-encephologram (EEG) parameters, etc. The second parameters may be used to determine range of motion values, activity levels, pain levels, and/or other evaluated parameters. The received signals and/or the determined information may be forwarded to the monitoring device 158 for evaluation and/or for display on the screen of the monitoring device 158.

The sensors 152 may be of various type and style. The sensors 152 may be patch type sensors and/or may be implantable type sensors. One patch type sensor is shown as being located on a chest of a patient in FIG. 3. Multiple implantable type sensors, which are located along, adjacent to and/or attached to a spine of the patient, are shown in FIG. 3. The sensors may be incorporated in hardware (e.g., spinal hardware) implanted in the patient, such as in screws or other implantable hardware. Other types of sensors and/or configurations of the sensor 152 may be incorporated in the wireless monitoring system 150. The sensors 152 may include respective pins and/or needles that are inserted into, for example, muscle tissue of a patient. The sensors 152 may be adhered to skin of a patient over, for example, muscle tissue.

The sensors 152 may continuously monitor activity and quality of sleep and as a result perform as surrogate sensors for RoM and pain. The sensors 152 may be leveraged for Pre-Op baseline determination and Post-Op outcome determination. As a couple of examples, the activity may be characterized as sedentary, light, medium, vigorous and/or may be indicated as a score between 1-10. The RoM may be based on reference points (or landmarks) and known spacing between the reference points. Vital signs such as heart rate and respiration rate may be monitored. The sensors 152 may include an interface and/or display for interaction with a user.

The sensors 152 may include accelerometers, temperature sensors, and/or other non-intrusive sensing elements. The accelerometers may include piezoelectric elements and perform low-pass filtering on generated signals. The sensors 152 may, for example, be used to detect the first parameters including voltage potentials and/or current levels passed between electrodes and/or pins of the sensors 152. The sensors 152 may be intrusive or non-intrusive sensors. The intrusive sensors may include one or more arrays of pins and/or needles for insertion into the patient. The non-intrusive sensors may include electrodes that rest on the skin of the patient and/or other sensing elements. Voltage potentials, impedances, and/or current levels between selected pairs of the pins, electrodes and/or needles may be monitored. This may include monitoring various pin, electrode, and/or needle combinations in a single array and/or pin, electrode, and/or needle combinations of pins electrodes, and/or needles in different arrays. For example, a voltage potential between a first pin, electrode and/or needle in a first array and a second pin, electrode and/or needle in a second array may be monitored. The sensors 152 may each include any number of pins, electrodes and/or needles. The sensors 152 may alert the CIM and/or the monitoring device 158 of nerve and/or muscle activity. The wireless monitoring system 150 may include any number of sensors and/or stimulation probe devices.

The wireless monitoring system 150 may also include a cloud (or network) 166. The cloud 166 may include a server 168. The server 168 may be located at a call center and/or be in communication with a call center. The communication may be via wires or a wireless link (e.g., a near field communication (NFC) telemetry link) may include a way station, an Internet link, a cell phone network connection, a universal serial bus (USB) connection, and/or other connections. The server 168 and/or call center may be centrally located and monitor information from the sensors 152 and/or information generated and/or provided by the monitoring device 158. The server 168 may communicate with the monitoring device 158. This communication may include transfer of data collected from the sensors 152 and/or other information collected via the systems of FIGS. 1-2B. For example, sensor data and/or image data may be provided by the monitoring device 158 to the server 168. The server 168 may analyze the data and feedback results of the analysis to the monitoring device 158 or the monitoring device 158 and/or CIM 202 may perform the analysis. The analyzing of the data may include motion/displacement measurements, spinal instability and/or alignment values/scores, RoM and/or pain scores, cumulative RoM and/or pain scores, overall combined scores, probabilities of a successful outcome of one or more procedures, etc. Examples of how RoM and pain scores, cumulative RoM and pain scores, and overall combined scores may be determined are further described below with respect to the embodiments of FIGS. 8-10. The results of the analysis may be transmitted from the server 168 to the monitoring device 158 and/or to other devices connected to and/or in a network of the server 168. The monitoring device 158 and/or the other devices may be implemented as cellular phones, tablets, computers, and/or other smart device. The sensors 152 may communicate with the other devices in addition to communicating with the monitoring device 158. The other devices may then perform similar analysis of data collected from the sensors 152. The sensors 152 may be incorporated in one or more wearable items that are worn on a patient (e.g., an adhesive bandage, a bracelet, cloths, etc.).

Referring now to FIGS. 3-4, which show a sensing module 200, a CIM 202 and the monitoring device 158. The sensing module 200 wirelessly communicates with the CIM 202 and/or with the monitoring device 158 via the CIM 202. The sensing module 200 may be included in any of the sensors disclosed herein including the sensors shown in FIG. 3. The CIM 202 may be included in the WIA 156 of FIG. 3.

The sensing module 200 includes a control module 206 (e.g., a microprocessor), a memory 208, and a physical layer (PHY) module 210 (e.g., a transceiver and/or radio). The control module 206 detects (i) signals from non-intrusive sensing elements 211, (ii) electromyographic signals generated in tissue of a patient via sensing elements 212 (e.g., pins, needles, electrodes, and/or flexible circuit with electrodes), (iii) voltage potentials, current levels, and/or impedances between selected pairs of the sensing elements 212. The electromyographic signals may be in the form of voltage signals having voltage potentials. One or more of the voltage signals and/or current levels may be from photodiodes and/or photodetectors, which may be included in the sensing elements 212. The control module 206 may also drive illuminating devices 214 (e.g., lasers, light emitting diodes (LEDs), etc.). The voltage signals and/or current levels generated via the photodiodes and/or photodetectors may be light emitted by the illuminating devices 214 and reflected off of tissue of a patient and detected by the photodiodes and/or photodetectors. The photodiodes may be used to detect color and/or wavelength of reflected light. Oxygen content levels may be determined based on amplitudes of the voltage signals generated by the photodiodes.

The control module 206 includes a front end receive module 216, a front end transmit module 218, and a baseband module 220. The front end receive module 216 may include one or more of each of an amplifier, a modulator, a demodulator, a filter, a mixer, a feedback module, and a clock. The front end transmit module 218 may include one or more of each of a modulator, an amplifier, and a clock. The baseband module 220 may include an upconverter and a downconverter. The front end receive module 216 may modulate, demodulate, amplify, and/or filter signals received from the sensing elements 211, 212 prior to generating an output for the baseband module 220. The front end transmit module 218 may transmit stimulation signals to selected ones of the sensing elements 212 (e.g., selected pins and/or needles) and/or control operation of the illuminating devices 214. The front end transmit module 218 may modulate stimulation signals provided to the sensing elements 212 and/or modulate illumination signals generated by the illuminating devices 214. Stimulation signals and/or illumination signals may not be modulated.

The filtering performed by the front end transmit module 218 may include bandpass filtering and/or filtering out (i) frequencies of the amplified signals outside of a predetermined frequency range, and (ii) a direct current (DC) voltage. This can eliminate and/or minimize noise, such as 60 Hz noise. The front end receive module 216 generates baseband signals based on the signals received by the front end receive module 216.

The baseband module 220 may include an analog-to-digital (A/D) converting module 230 (e.g., an A/D converter) and convert the baseband signals (analog signals) to digital baseband (BB) signals. The BB module 220 and/or the A/D converting module 230 may sample the output of the front end receive module 216 at a predetermined rate to generate frames, which are included in the digital BB signals. By A/D converting signals at the sensor as opposed to performing an A/D conversion at the CIM 202 or the monitoring device 158, opportunities for signal interference is reduced. The BB module 220 may include a multiplexer 232 for multiplexing (i) signals generated by the front end receive module 216, and/or (ii) generated based on the signals generated by the front end receive module 216.

The BB module 220 may then upconvert the digital BB signal to an intermediate frequency (IF) signal. The BB module 220 may perform direct-sequence spread spectrum (DSSS) modulation during upconversion from the digital BB signal to the IF signal. The BB module 220 may include a mixer and oscillator for upconversion purposes. The BB module 220 and/or the control module 206 may compress and/or encrypt BB signals transmitted to the PHY module 210 prior to upconverting to IF signals and/or may decompress and/or decrypt signals received from the PHY module 210. The PHY module 210 may communicate with other electronic devices using near field communication protocols.

The BB module 220 may provide a received signal strength indication (RSSI) indicating a measured amount of power present in a RF signal received from the CIM 202. This may be used when determining which of multiple CIMs the sensor is to communicate with. The control module 206 may select a CIM corresponding to a SYNC request signal and/or a payload request signal having the most power and/or signal strength. This may include (i) selecting a channel on which the SYNC request signal and/or the payload request signal was transmitted, and (ii) communicating with the CIM on that channel. This allows the control module 206 to select the closest and proper CIM. This selection may be performed when the sensor has not previously communicated with a CIM, is switching to a different WNIM network, and/or has been reset such that the sensor does not have a record of communicating with a CIM. In one embodiment, the sensors are unable to be reset.

The memory 208 is accessed by the control module 206 and stores, for example, parameters 240. The parameters 240 may include parameters provided in SYNC request signals and/or parameters associated with signals generated via the sensing elements 211, 212. The parameters may include parameters determined by the control module 206. The parameters stored in the memory 208 may include voltages, current levels, amplitudes, peak magnitudes, pulse durations, temperatures, pH levels, frequencies, impedances, resistances, oxygen levels, perfusion and/or conduction rates, accelerations, heart rates, blood pressures, ECG parameters, respiratory parameters, body activity values, heart sounds, blood gas pH, red blood cell counts, white blood cell counts, EEG parameters, etc.

The PHY module 210 includes a transmit path 242 (or transmitter) and a receiver path 246 (or receiver). The transmit path 242 includes a modulation module 248 (e.g., a modulator) and an amplification module 250 (e.g., an amplifier). The modulation module 248 modulates and upconverts the IF signal to generate a radio frequency (RF) signal. This may include Gaussian frequency-shift keying (GFSK) modulation. The modulation module 248 may include, for example, a filter, a mixer, and an oscillator (collectively identified as 252). The amplification module

250 may include a power amplifier 254, which amplifies the RF signal and transmits the RF signal via the antenna 256.

The receiver path 246 includes a second amplification module 260 and a demodulation module 262 (e.g., a demodulator). The amplification module 260 may include a low-noise amplifier (LNA) 264. The second amplification module 260 amplifies RF signals received from the CIM 202. The demodulation module 262 demodulates the amplified RF signals to generate IF signals. The IF signals are provided to the BB module 220, which then downconverts the IF signals to BB signals. The demodulation module 262 may include, for example, a filter, a mixer, and an oscillator (collectively identified as 266). The A/D converting module 230 may include a digital-to-analog (D/A) converter to convert the BB signals to analog signals. The RF signals received from the CIM 202 may include, for example, SYNC request signals or portions thereof.

The CIM 202 includes a PHY module 300, a control module 302, a memory 304, and the interface 163 (e.g., 32 pin connector). The PHY module 300 includes a receive path (or receiver) 308 and a transmit path (or transmitter) 310. The receive path 308 includes an amplification module 312 and a demodulation module 314. The amplification module 312 amplifies RF signals received from the sensing module 200 and/or from other sensor modules. The amplification module 312 may include a LNA 315. The demodulation module 314 demodulates and downconverts the amplified RF signals to generate IF signals. The demodulation module 314 may include a filter, mixer, and an oscillator (collectively referred to as 317). The transmit path 310 includes a modulation module 316 and an amplification module 318. The modulation module 316 modulates and upconverts IF signals from the control module 302 to generate RF signals. This may include Gaussian frequency-shift keying (GFSK) modulation. The modulation module 316 may include, for example, a filter, a mixer, and an oscillator (collectively identified as 319). The amplification module 318 transmits the RF signals to the sensing module 200 via an antenna 320 and/or to other sensor modules and/or stimulation probe devices. The amplification module 318 may include a power amplifier 321.

The control module 302 includes a BB module 324 and a filtering module 326. The BB module 324 converts IF signals received from the PHY module 300 to BB signals and forwards the BB signals to the filtering module 326. The BB module may demultiplex an IF signal and/or a BB signal to provide multiple IF signals and BB signals. The BB module 324 also converts BB signals from the filtering module 326 to IF signals, which are forwarded to the modulation module 316. The BB module 324 may include a D/A converting module 328, a demultiplexer 329, and/or a fast Fourier transform (FFT) module 331.

The D/A converting module 328 may include an A/D converter to convert analog signals from the filtering module 326 to digital signals. The D/A converting module 328 may include a D/A converter to convert digital signals from the PHY module 300 to analog signals. In one embodiment, the BB module 324 does not include the D/A converting module 328 and digital signals are passed between the filtering module 326 and the PHY module 300. The demultiplexer 329 may demultiplex the analog signals and/or the digital signals. The FFT module 331 performs a FFT of the analog signals and/or the digital signals for spectral waveform analysis including frequency content monitoring.

The BB module 324 may attenuate signals received from the demodulation module 314. The filtering module 326 may be a bandpass filter and remove frequencies of signals outside a predetermined range and/or DC signals. This can eliminate and/or minimize noise, such as 60 Hz noise. The BB module 324 and/or the control module 302 may compress and/or encrypt signals transmitted to the modulation module 316 and/or decompress and/or decrypt signals received from the demodulation module 314. Although the CIM 202 is shown as being connected to the monitoring device 158 via the interface 163, the CIM 202 may be separate from the monitoring device 158 and wirelessly communicate with the monitoring device 158 via the PHY module 300.

The memory 304 is accessed by the control module 302 and stores, for example, parameters 330. The parameters 330 may include parameters provided in SYNC request signals and/or parameters indicated in and/or generated based on the signals received via the sensing elements 211, 212. The parameters 330 may include The parameters stored in the memory 208 may include voltages, current levels, amplitudes, peak magnitudes, pulse durations, temperatures, pH levels, frequencies, impedances, resistances, oxygen levels, perfusion and/or conduction rates, accelerations, heart rates, blood pressures, ECG parameters, respiratory parameters, body activity values, heart sounds, blood gas pH, red blood cell counts, white blood cell counts, EEG parameters, etc. and may include or be the same as the parameters 240. The memory 304 may also store synchronization requests 332, which are defined below.

The monitoring device 158 may include a control module 340, a PHY module 342, a CIM interface 344, a display 346 and a memory 348. The control module 340: generates payload request signals; receives data payload signals from the sensing module 200 and/or other sensing modules and stimulation probe devices via the CIM 202; and displays signals and/or other related information on the display 346. The displayed signals and/or information may include the parameters 330 and/or information generated based on the parameters 330. The PHY module 342 may transmit signals to and receive signals from the control module 340 via the interfaces 163, 344 as shown or wirelessly via an antenna (not shown). The memory 348 is accessed by the control module 340 and stores the parameters 330 and may store payload requests 350, which are defined below. The control module 302 and/or the control module 340 may include the procedure module 162.

The control modules 206, 326, the BB modules 220, 324, the PHY modules 210, 300, and/or one or more modules thereof control timing of signals transmitted between the sensing module 200 and the CIM 202. The PHY modules 210, 300 may communicate with each other in a predetermined frequency range. As an example, the PHY modules 210, 300 may communicate with each other in 2.0-3.0 giga-hertz (GHz) range. In one embodiment, the PHY modules 210, 300 transmit signals in a 2.4-2.5 GHz range. The PHY modules 210, 300 may communicate with each other via one or more channels. The PHY modules 210, 300 may transmit data at predetermined rates (e.g., 2 mega-bits per second (Mbps)). The CIM 202 and/or the monitoring device 158 may set the frequency range, the number of channels, and the data rates based on: the number of sensor modules in and actively communicating in the wireless monitoring system 150; the types of the sensors; the number of channels per sensor; and/or the speed per channel of each of the sensors.

Figure 5:
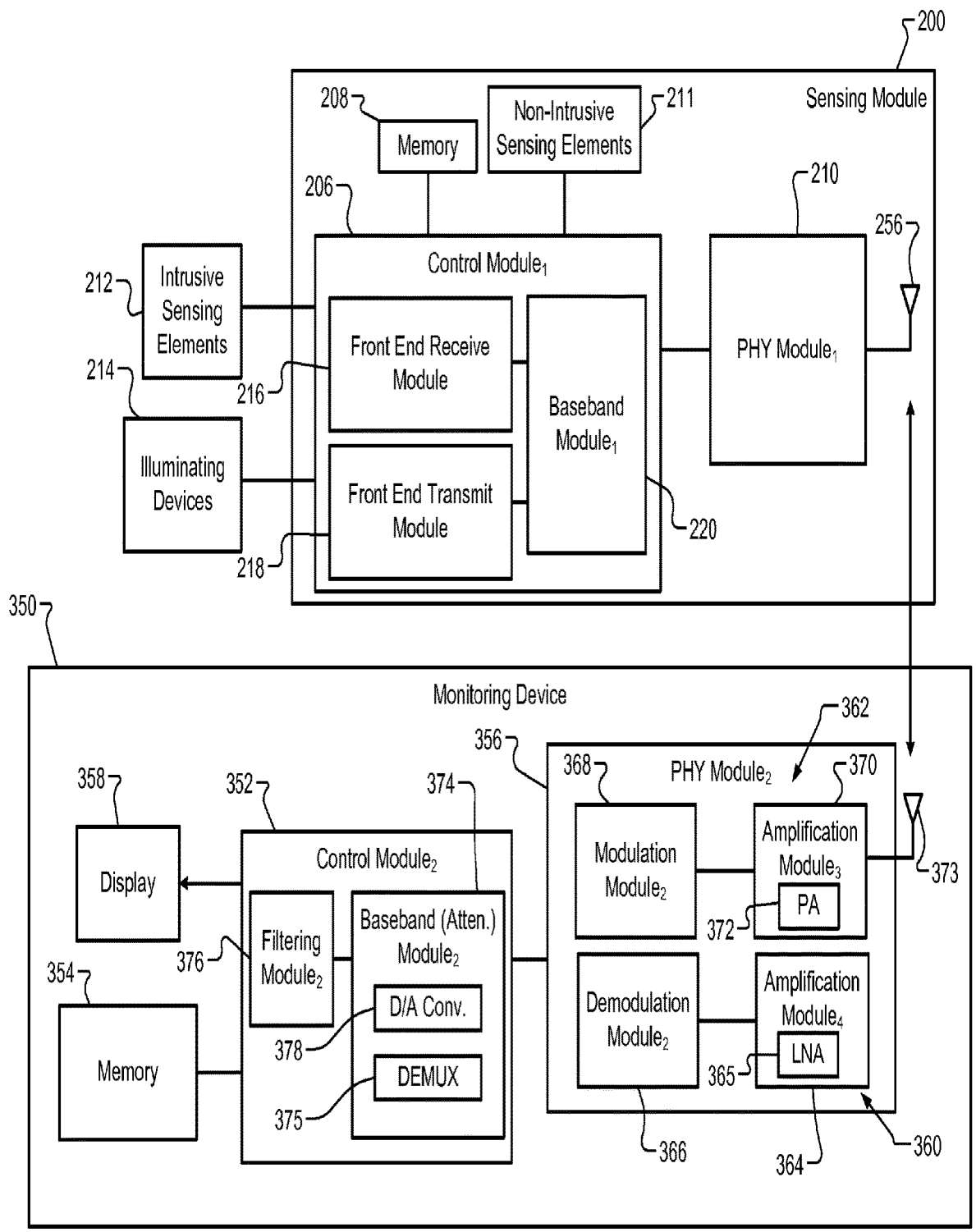
FIG. 5 is a functional block diagram of another sensing module and another monitoring device in accordance with the present disclosure.

Referring now to FIG. 3 and FIG. 5, which shows the sensing module 200 and a monitoring device 350. The sensing module 200 includes the control module 206, the memory 208 and the PHY module 210. The control module 206 includes the front end receive module 216, the front end transmit module 218, and the BB module 220. The control module 206 receives signals from the sensing elements 211, 212 and controls operation of the illuminating devices 214. The control module 206 reports data associated with the signals to the monitoring device 350 via the PHY module 210. The control module 206 also receives signals (e.g., synchronization request signals) from the monitoring device 350 via the PHY module 210.

The monitoring device 350 includes a control module 352, a memory 354, a PHY module 356, and the display 358. Functionality of the CIM 202 of FIG. 4 is included in the monitoring device 350. The PHY module 356 includes a receive path 360 (or receiver) and a transmit path 362 (or transmitter). The receive path 360 includes an amplification module 364 and a demodulation module 366. The amplification module 364 via a LNA 365 amplifies RF signals received from the sensing module 200 and/or from other sensor modules and/or stimulation probe devices. The demodulation module 366 demodulates and downconverts the amplified RF signals to generate IF signals. The transmit path 362 includes a modulation module 368 and an amplification module 370. The modulation module 368 and the amplification module 370 may operate similar to the modulation module 316 and the amplification module 312. The amplification module 370 may include a power amplifier 372 and transmits RF signals via an antenna 373 to the sensing module 200 and/or to other sensor modules.

The control module 352 includes a BB module 374 and a filtering module 376. The BB module 374 converts IF signals received from the PHY module 356 to BB signals and forwards the BB signals to the filtering module 376. The BB module 374 may demultiplex the IF signals and/or the BB signals. The BB module 374 also converts BB signals from the filtering module 376 to IF signals, which are forwarded to the modulation module 368. The BB module 374 may include a D/A converting module 378 and/or a demultiplexer 375. The D/A converting module 378 may include an A/D converter to convert analog signals from the filtering module 376 to digital signals. The demultiplexer 375 may demultiplex the analog and/or the digital signals. The D/A converting module 378 may include a D/A converter to convert digital signals from the PHY module 356 to analog signals. In one embodiment, the BB module 374 does not include the D/A converting module 378 and digital signals are passed between the filtering module 376 and the PHY module 356. The BB module 374 may attenuate signals received from the demodulation module 366. The filtering module 376 may be a bandpass filter and remove frequencies of signals outside a predetermined range and/or DC signals. This can eliminate and/or minimize noise, such as 60 Hz noise. The BB module 374 and/or the control module 352 may compress and/or encrypt signals transmitted to the modulation module 368 and/or decompress and/or decrypt signals received from the demodulation module 366.

Referring now to FIGS. 3 and 5, the BB module 220 of the sensing module 200 may provide a received signal strength indication (RSSI) indicating a measured amount of power present in a RF signal received from the monitoring device 350. This may be used when determining which of multiple monitoring devices to communicate with. The control module 206 may select a monitoring device corresponding to a SYNC request signal and/or a payload request signal that has the most power and/or signal strength. This may include selecting a channel on which the SYNC request signal and/or the payload request signal was transmitted and communicating with the CIM 202 and/or the monitoring device 350 on that channel. This allows the control module 206 to select the closest and proper monitoring device. This selection may be performed when the corresponding sensor has not previously communicated with the monitoring device 350 and/or other monitoring devices and/or has been reset such that the sensor does not have a record of communicating with the monitoring device 162 and/or other monitoring devices.

The memory 354 may store the parameters 330, payload requests 351 and/or the SYNC requests 332. The memory 354 may store the SYNC requests 332 and may not store the payload requests 351. This is because the monitoring device 350 may generate SYNC requests and not payload requests.

Figure 6:
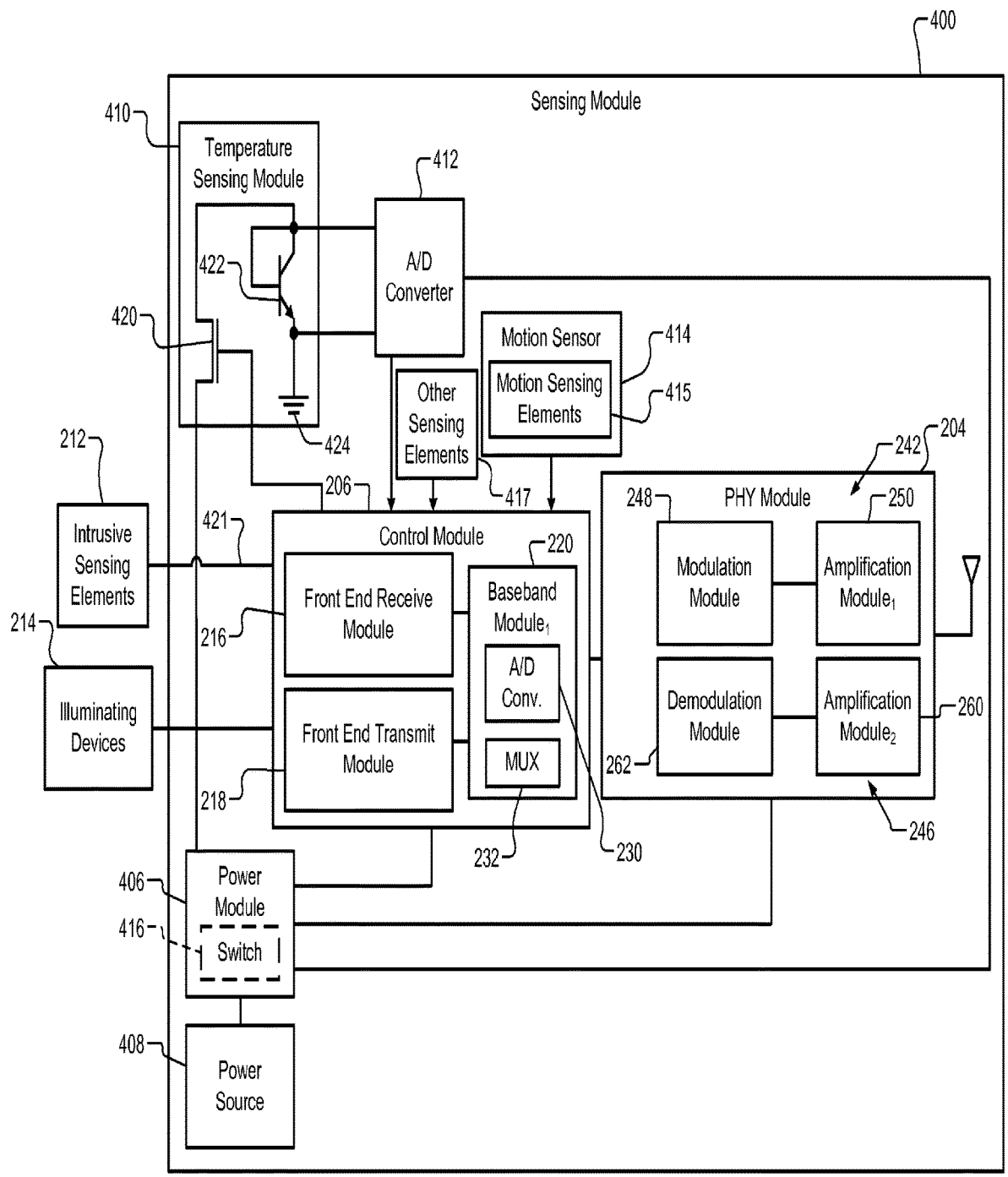
FIG. 6 is a functional block diagram of another sensing module in accordance with the present disclosure.

Referring now to FIGS. 3 and 6, which show a sensing module 400. The sensing module 400 may be included in any of the sensors (e.g., the sensors 152 of FIG. 3) disclosed herein and/or replace any of the sensing modules (e.g., the sensing module 200 of FIGS. 4-5) disclosed herein. The sensing module 400 may include the control module 206, the PHY module 210, a power module 406, a power source 208, a temperature sensing module 410, an A/D converter 412, and an accelerometer 414 (e.g., a 3-axis accelerometer or 9-axis accelerometer) or other motion sensor (e.g., a gyro). The motion sensor 414 includes motion sensing elements (e.g., electrodes) 415 for generating a signal indicative of motion and/or acceleration. Although the sensing module 400 is shown as having the temperature sensing module 410, the sensing module 400 may not include the temperature sensing module 410. The temperature sensing module 410 may be replaced with a temperature sensor, such as an infrared temperature sensor. In one embodiment, the sensing module 400 includes the temperature sensing module 410 and the temperature sensor. Although shown separate from the control module 206, the PHY module 210, the power module 406, the temperature sensing module 410 and/or the A/D converter 412 may be included in and as part of the control module 206. The sensing module 400 may include or be connected to other sensing elements 417.

The control module 206 includes the front end modules 216, 218 and the BB module 220 of FIG. 4. The PHY module 210 includes the modulation module 248, the demodulation module 262 and the amplification modules 250, 260 of FIG. 4.

The control module 206, the PHY module 210, the temperature sensing module 410, and the A/D converter 412 operate based on power from the power module 406. The power module 406 receives power from the power source (e.g., a battery). The power module 406 may include a switch 416 as shown (or a pull-tab) to turn ON and/or OFF the power module 406 and thus turn ON and/or OFF the sensing module 400 and/or the corresponding sensor. The switch 416 may be manually operated or may be operated by the power module 406, the control module 206 and/or the PHY module 210. In one embodiment, the switch 416 is manually operated and at least partially exposed on an exterior of the sensing module 400 and/or corresponding sensor housing. In another embodiment, the switch 416 includes one or more transistors located in the control module 206, the PHY module 210, and/or in the power module 406, as shown. If included in one of the modules 206, 210, 406, the switch 416 is not exposed on an exterior of the sensing module 400 and/or the corresponding sensor housing. The state of the switch 416 may be controlled by the control module 206, the PHY module 210, and/or the power module 406 based on signals received from sensing elements 211, 212, the CIM 202, and/or the monitoring device 350 of FIGS. 4-5. The sensing elements 211 may include the temperature sensing module 410 and the motion sensor 414. Transitioning the switch 416 via one of the modules 206, 210, 406 from a first state to a second state to turn ON at least a portion of the sensor and/or at least a portion of the one or more of the modules 206, 210, 406 may be referred to as an "auto-start".

The sensing module 400 may operate in: a high power mode (fully powered mode), a low (or idle) power mode (partially powered or transmitting less frequently then when in the high power mode), a sleep mode, or OFF. Operation in and transition between these modes may be controlled by one or more of the modules 206, 210, 406. As an example, the sensor may be OFF (or dormant) while being shipped and/or not in use. The sensor may also be OFF if: not yet communicated with a CIM and/or monitoring device; a connection has not yet been established between the sensing module 400 and a CIM and/or monitoring device; the sensor has not yet been assigned to a CIM and/or monitoring device; and/or the sensor has not yet been assigned one or more time slots in which to communicate with a CIM and/or monitoring device.

Transitioning to the low power mode, the sleep mode and/or to OFF decreases power consumption and can aid in minimizing size of the power source 408. The power source may include a solid-state rechargeable power source. While partially powered, the control module 206 and/or portions of the control module 206 and the PHY module 210 may be deactivated. The receiver path of the PHY module 210 may remain activated to (i) receive signals from the CIM 202 and/or portions of the control module 206, and (ii) detect signals from the sensing elements 211, 212. The transmit path 242 of the PHY module 210 and/or other portions of the sensor that are not experiencing activity may be deactivated. Transitioning between the stated modes is further described below.

Referring again to FIGS. 3 and 6, one or more of the sensors 152 may include a temperature sensing module (e.g., the temperature sensing module 410) and/or a motion sensor (e.g., an accelerometer, a gyro sensor, or the motion sensor 414). By including temperature sensing modules in sensors, temperatures of various points on a patient may be monitored.

The temperature sensing module 410 may include a first transistor 420 and a second transistor 422. The first transistor 420 may be transitioned between states to supply current to the second transistor 422. This turns ON the temperature sensing module 410. The second transistor 422 is configured to detect a temperature. As an example, the first transistor 420 may be a metal-oxide-semiconductor field-effect transistor (MOSFET) and includes a drain, a gate and a source. The second transistor 422 may be a bipolar junction transistor (BJT) and includes a collector, a base and an emitter. The transistors 420, 422 are shown for example purposes only, one or more of the transistors 420, 422 may be replaced with other transistors or other similarly operating circuitry. The drain is connected to and receives current from the power module 406. The gate is connected to and receives a control signal from the control module 206. The source of the first transistor 420 is connected to the collector and the base. The collector is connected to a ground terminal 424. The collector and the emitter are also connected to the A/D converter 230.

The second transistor 422 is connected in a diode configuration. Temperature dependence of the base-to-emitter voltage (Vbe) is the basis for temperature measurement. The base-to-emitter voltage Vbe is dependent on temperature while (i) the power source 408 and the power module 406 supply a constant level of current to the collector via the first transistor 420, and (ii) a voltage across the base and the collector is zero. The voltage across the base (or collector) and the emitter is detected by the A/D converter. The detected voltage is converted to a temperature via the control module 206. The control module 206 based on a digital signal output by the A/D converter 230, determines the temperature. The temperature may be determined using, for example, expression 1, where A is a predetermined multiplier constant and B is a predetermined offset constant.

$$A \cdot Vbe + B \quad [1]$$

In addition to detecting signals from the sensing elements 211, 212 and temperature, the sensing module 400 may also detect other parameters, such as heart rate, respiration rate, and/or muscle spasms. These parameters may be determined via one or more of the control modules 206, 302, 340, 326 of the sensor, the CIM 202 and the monitoring devices 158, 350 of FIGS. 3-5. The monitoring devices 158, 350 may generate an alert signal and/or display these parameters on the display 358. This information may also be used to provide an early indication that a patient is coming out from anesthesia prematurely. The sensing elements 211, 212 may be monitored for EMG purposes as well as for heart rate, respiration rate, and/or muscle spasms purposes. To detect this information, the sensor may be attached to (or mounted on) a trunk of a patient or may be implanted in the patient.

A heart rate may be in a same frequency band as an electromyographic signal. A heart rate is periodic unlike an electromyographic signal. A voltage potential detected as a result of a beating heart may have a larger amplitude (or magnitude) than amplitudes (or magnitudes) of an electromyographic signal. A respiration rate is typically in a lower frequency band than an electromyographic signal. A muscle spasm may have a distinguishable frequency and/or distinguishable frequency band. Thus, one or more of the control modules 206, 302, 340, 326 may distinguish between signals or portions of signals corresponding to a heart rate, a respiration rate, and an electromyographic signal based on these differences. If the control module 206 of the sensor detects heart rate, respiration rate, and/or muscle spasms, the control module 206 may wirelessly transmit this information to the CIM 202 and/or one of the monitoring devices 158, 350. The monitoring devices 158, 350 may then display this information and/or generate an alert signal if one or more of these parameters are outside of respective predetermined ranges and/or thresholds.

In addition to or as an alternative to monitoring the sensing elements 211, 212 to detect heart rate, respiration rate, and/or muscle spasms, the sensor includes a motion sensor. As similarly described above, one or more of the control modules 206, 302, 340, 326 may monitor signals from the motion sensor (e.g., acceleration signals generated by an accelerometer) to detect activity of muscle firing, heart rate, respiration rate, and/or muscle spasms. The acceleration information, muscle firing activity, heart rate, respiration rate, and/or muscle spasm information determined based on the acceleration signals may be wirelessly transmitted from the sensor and/or PHY module 210 to the CIM 202 and/or one of the monitoring devices 158, 350.

The sensor may "self-awake". In other words, the sensor may automatically transition from being OFF or being in the low power (or sleep) mode to being powered ON and being in the high power mode when attached to a patient. For example, while not attached to a patient, there is an "open" circuit between two of the sensing elements 212. Thus, an impedance between two of the sensing elements 212 is high (e.g., greater than 10 kilo-Ohms (kOhms)). Subsequent to attaching the sensor to the patient, an impedance between the two of the sensing elements 212 is low (e.g., less than 1 kOhms) and/or significantly less then when the sensor was not attached. This difference in impedance can be detected and cause the power module 406 and/or the control module 206 to switch operating modes.

In another embodiment, the two of the sensing elements 212 and corresponding impedance between the two of the sensing elements 212 operate as a switch to activate the power module 406. Upon activation, the power module 406 may supply power to the control module 206 and/or the PHY module 210.

In yet another embodiment, the power module 406 (or analog front end) is configured to generate a DC voltage while the sensor is not attached to a patient. Generation of the DC voltage may be based on the impedance between the two of the sensing elements 212. This DC voltage is detected by the control module 206. The control module 206 remains in the low power (or sleep) mode while receiving the DC voltage. The power module 406 ceases to provide the DC voltage when the electrodes are attached to the patient. This causes the control module to transition (i) from being OFF to being in the low power mode or high power mode, or (ii) from being in a sleep mode to being in the low power mode or the high power mode.

The control module 206 and/or the power module 406 may periodically transition between operating in a low power (or sleep) mode and the high power mode to check the impedance between the two of the sensing elements 212 and whether the DC voltage is provided. This may occur every predetermined period (e.g., 30-60 seconds). In another embodiment, in response to the two of the sensing elements 212 being attached to a patient, the power module 406 may transition (i) from not supplying power to the control module 206, the PHY module 210 and/or portions thereof to (ii) supplying power to the control module 202, the PHY module 210 and/or portions thereof.

Although the modules 210, 406, 410 and the A/D converter 230 are shown as being separate from the control module 206, one or more of the modules 210, 406, 410 and the A/D converter 230 or portions thereof may be incorporated in the control module 206. Signal lines 421 are shown between the sensing elements 212 and the control module 202. A third signal line may be included for noise feedback cancellation.

The sensing elements 211 may include other sensors and/or sensing elements 450, such as one or more of each of an infrared sensing element, a pH sensor, a sensing array, a photodiode detector, etc. In one embodiment, the pins of the sensing arrays are used to detect voltages, current levels, impedances, and/or resistances. In another embodiment, one of the sensing arrays is used to detect voltages, current levels, impedances, and/or resistances while the other sensing array is used to provide stimulation pulses. In yet another embodiment, selected pins of each of the sensing arrays are used to detect voltages, current levels, impedances, and/or resistances while the same and/or other selected pins of the sensing arrays are used to provide stimulation pulses.

The infrared sensing elements (e.g., diodes capable of detecting infrared energy) may be part of an infrared temperature sensor and detect temperature of tissue and generate temperature signals indicative of the temperature. The infrared temperature sensor may detect infrared energy emitted from the tissue within a predetermined infrared band. As a nerve is decompressed, perfusion occurs, which increases blood flow and oxygen levels and as a result increases temperature of the tissue of and around the nerve. Thus, the temperature of the tissue is indicative of the state of decompression and/or level of perfusion of the tissue. In addition or as an alternative to the infrared temperature sensor a heat sensitive camera may be used to monitor small temperature changes associated with changes in perfusion.

The pH sensor (or neuropathy sensor) may include a needle and a flex circuit. The pH sensor detects pH levels in tissue of a patient. The needle may be inserted in the tissue when the sensor is attached to the tissue. The needle guides the flex circuit into the patient. The flex circuit may include pH sensing elements (e.g., electrodes 319) between which current is supplied. The flex circuit performs electrochemical impedance spectroscopy techniques to measure pH levels of target tissue. This may include supplying current to the electrodes and monitoring changes in conductivity levels of the tissue. Presence of different chemicals in the tissue changes impedance of the tissue and as a result conductivity of the tissue. For example, if tissue of a patient exhibits poor perfusion, the patient may develop neuropathy (or diabetic neuropathy due to lack of blood flow), which includes accumulation of nitrous oxide and associated chemicals with nitrogen. This results in an acidic reaction that is directly related to a pH level, which can be detected using the flex circuit.

The sensing array may include a vertical-cavity surface-emitting laser (VCSEL) and a photodiode detector (or other light detecting device) or other optical and/or perfusion sensor. The VCSEL and the photodiode detector may be used to detect changes in wavelength of light reflected off of tissue and/or blood. The changes in wavelength correspond to changes in color, which relates to changes in blood flow, pressure of blood flow, and/or oxygen levels in the blood. As more blood flows the pressure of the blood flow increases, which provides an increase in a pulsified amplitude of a received signal. As another example, the more red the color of the reflected light, the more blood flowing in the tissue.

In addition to being used to detect the above-stated parameters, one or more of the pins may be used to detect temperature of tissue within the patient. Thus, each of the pins may be used for multiple purposes. The pins may be used for nerve integrity monitoring, perfusion monitoring, decompression monitoring, etc. Impedance of tissue changes during perfusion. This may be detected using the pins. Different sets of the pins may be used for different purposes or each set of the pins may be used for all of the stated purposes. The pins may be inserted in muscle/tissue being monitored. Each of the pins may be used for monitoring one or more parameters. In one embodiment, a respective number of pins are allocated for each parameter monitored. Each parameter monitored may have a same or different number of allocated pins.

Figure 7:
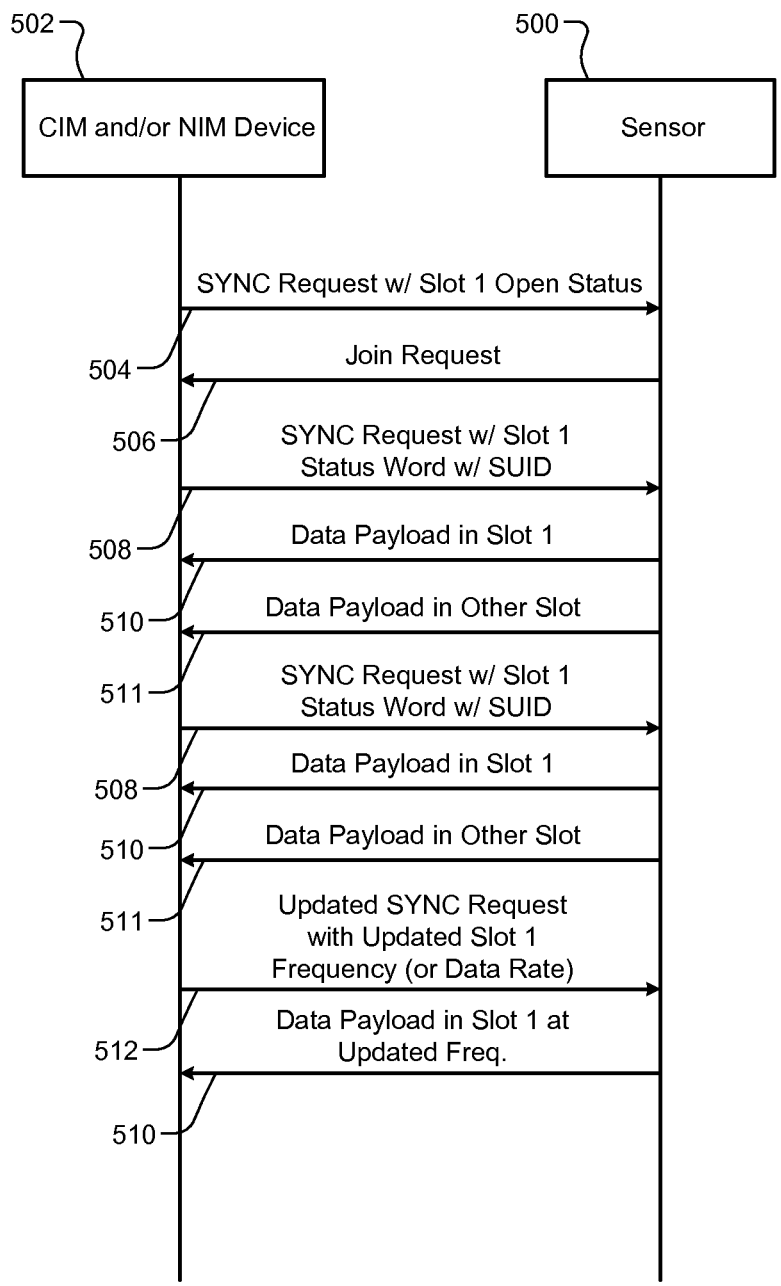
FIG. 7 is a signal flow diagram illustrating a sensor joining and communicating in a wireless monitoring system in accordance with the present disclosure.

Additional details of the wireless protocol are described below with respect to FIG. 7. FIG. 7 shows a signal flow diagram illustrating a sensor 500 joining a WNIM network and communicating in a WNIM system with a CIM and/or a monitoring device (collectively designated 502). The sensor 500 may refer to any sensor disclosed herein. Similarly, the CIM and/or monitoring device 502 may refer to any CIM and/or monitoring device disclosed herein. Before a sensor responds to a SYNC request with a data payload, a joining process is performed. Joining establishes a link between the sensor and a CIM and/or monitoring device and together the sensor and the CIM and/or monitoring device (and/or other sensors and/or stimulation probe devices linked to the CIM and/or monitoring device) provide a WNIM network. FIG. 7 shows an example sequence of events performed for the sensor 500 to join the WNIM network and also how different modes of operation are obtained.

A SYNC request signal 504 is transmitted from the CIM and/or NIM device 502 and includes a word for each time slot in a corresponding SYNC interval and is periodically and/or continuously updated and transmitted to indicate the statuses of the slots. To join the WNIM network, the sensor 500 checks all the available slots and selects the time slot in which to transmit a data payload signal to the CIM and/or NIM device 502. Prior to transmitting the data payload, the sensor 500 sends a join request 506 to join the WNIM network and communicate in the selected time slot. The join request 506 may be transmitted in the selected time slot and indicates a sensor unique identifier (SUID) of the sensor, the selected time slot, the type of the sensor, a minimum data rate, and/or a maximum data rate of the sensor. In one embodiment, the sensor 500 sends the SUID in the selected time slot and the CIM and/or NIM device 502 has a record of the type and data rates of the sensor.

Based on the join request 506, the CIM and/or NIM device 502 fills an appropriate slot status word with the SUID from the sensor 500. The CIM and/or NIM device 502 may then send an updated SYNC request 508 with the updated slot status word indicating designation of the selected time slot to the sensor 500. The sensor 500 receives the updated SYNC request with the SUID in the corresponding slot status word and responds by sending a data payload to the CIM and/or the NIM device 502 in the selected slot. If more than one slot is selected and/or designated to the sensor 500, the sensor 500 may transmit one or more data payloads in the slots selected and/or designated to the sensor 500 (data payloads in slot 1 are designated 510 and data payloads in other slots are designated 511). The time slots may be associated with one or more channels of the sensor 500. The transmission of the SYNC requests and the data payloads may be periodically transmitted over a series of periodic SYNC intervals (or RF frames).

Once linked to the CIM and/or NIM device 502, the sensor 400 may now be controlled by the CIM and/or NIM device 502 via transmission of updated SYNC requests. The CIM and/or NIM device 502 may control, for example, output data rates and transitions between power modes of the sensor 500. As an example, the CIM and/or NIM device 502 may update the output data rate from 10 kHz to 5 kHz for the time slot of the sensor 500 by transmitting an updated SYNC request 512. Sensors linked to the CIM and/or NIM device 502 inspect control bits (e.g., bits of the slot status words) in SYNC requests to determine respective operating and/or power modes. The sensors then transition to the indicated operating and/or power modes.

As described above, the CIMS, NIM devices, and sensors disclosed herein may communicate with each other using bits within payload requests, SYNCH requests, data payloads, and response signals. The CIMS and/or NIM devices may initiate communication by a sending a payload request (SYNC request). The data payload may include one 16-bit word for payload validation. The 16 bit-word may include a SUID. When the CIM and/or NIM device receives a data payload, the CIM and/or NIM device compares the SUID with an expected SUID stored in memory of the CIM and/or NIM device. The SUID may have been stored in the memory when the sensor joined the corresponding WNIM network. If the comparison indicates a match, the data in the data payload may be displayed at the NIM device.

Likewise, when the sensor receives the SYNC request, the sensor compares a console unique identifier (CUID) of the CIM and/or NIM device provided in the SYNC request with an expected CUID stored in a memory of the sensor. The CUID may have been stored in the memory when the sensor joined the corresponding WNIM network. If the comparison of the CUIDs indicates a match, the sensor may respond, depending on mode status bits within a slot status word of the SYNC request, with one or more data payloads in the appropriate time slots following the SYNC request. The mode status bits may be the bits of the slot status word indicating a data rate and/or whether a stimulation pulse is to be generated.

Range of Motion (RoM) and Pain Monitoring

RoM and pain are key variables for determining successful spinal surgery outcomes. RoM is a surrogate for patient activity. Pain is a surrogate for quality of sleep (QoS). RoM may be measured via imaging and measuring vertebrae displacement and/or curvature, for example, using the procedural operating system 15 and/or the spinal kinematics system of FIGS. 2A, 2B and generating a RoM score based on the measured vertebra displacements. Displacement of each vertebra of a spine may be measured relative to one or more reference points. The reference points may be marked or unmarked. Curvature of the spine may refer to (i) a size of a radius of an arc formed by the curvature of the spine, and/or (ii) how uniform the curvature of the spine is from vertebra-to-vertebra. As another example, the RoM score may be generated based on information received from the motion sensor 414 of FIG. 6. For example, outputs of one or more 3-axis or 9-axis accelerometers and/or other motion sensors may be used to determine an activity level, posture, and vertebrae positions over time. Output of the accelerometers may be integrated twice to provide position information. The RoM score may also be based on an ECG value, a respiration rate (RR), beats-per-minute (bpm) of a heart, heart rate variability, etc. An amount of pain may be indicated as a stress score, which may be generated based on sleep interruption (number of sleep interruptions within a predetermined period), ECG (heart rate variability) over the predetermined period, and respiration rates over the predetermined period.

Figure 8:
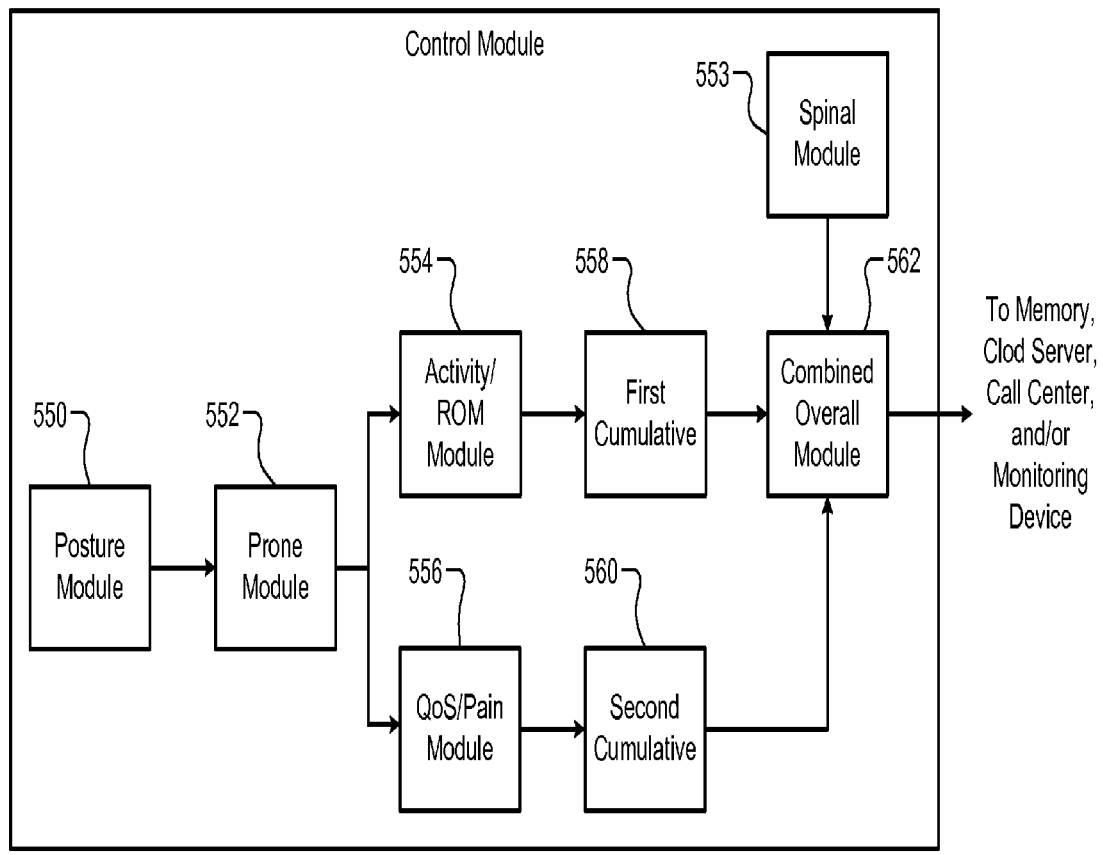
FIG. 8 is a view of a functional block diagram of a portion of a control module in accordance with an embodiment of the present disclosure.

FIG. 8 shows an example of a portion of a control module 548 (e.g. one of the control modules 302, 340, 352 of FIGS. 4-6). The control module 548 may include a posture module 550, a prone module 552, a spinal module 553, an activity and/or RoM module 554, a QoS and/or pain module 556, a first cumulative module 558, a second cumulative module 560, and a combined overall module 562. These modules are further described below with respect to the methods of FIGS. 9-10.

Figure 9:
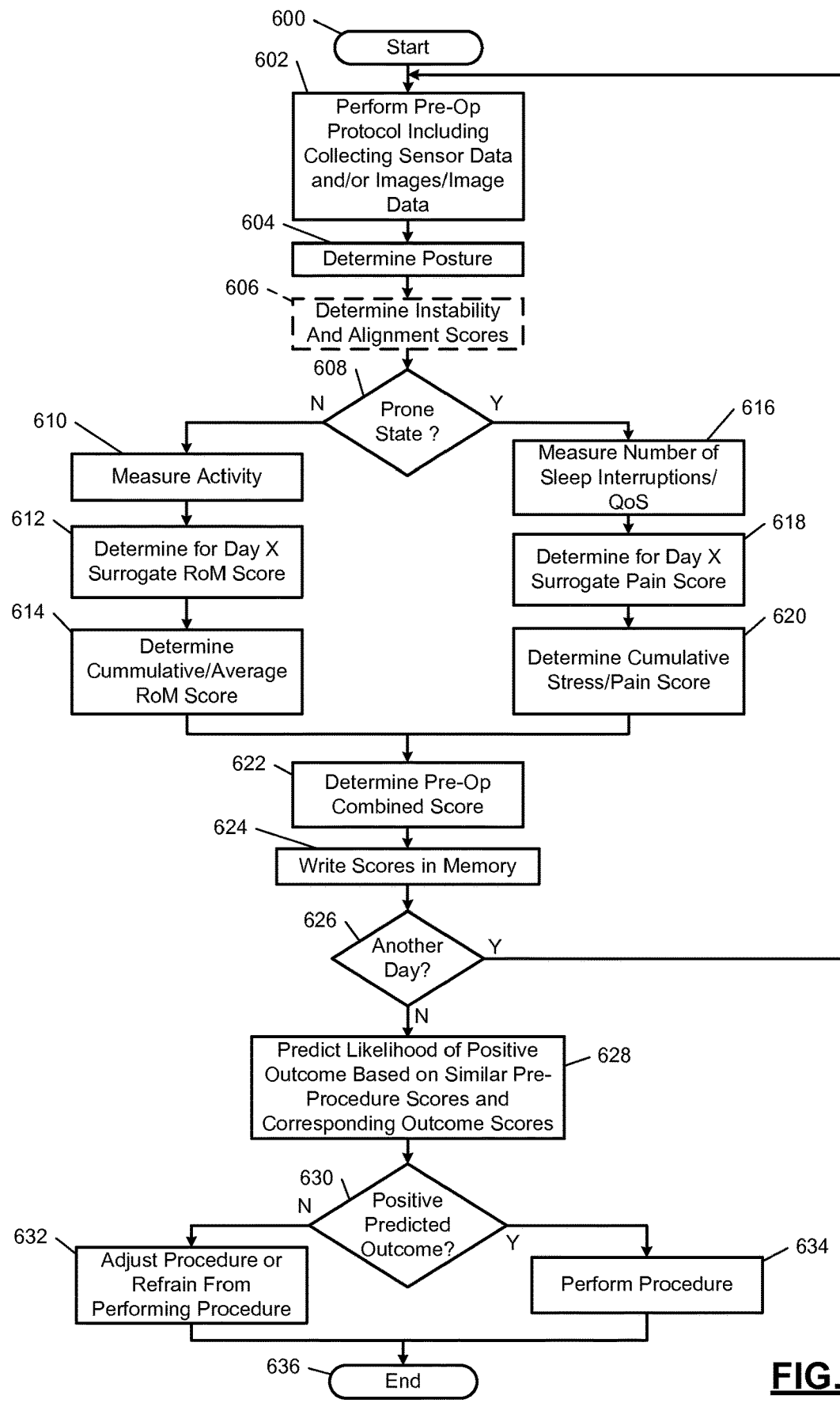
FIG. 9 illustrates a pre-operation (Pre-Op) method in accordance with the present disclosure.
Figure 10:
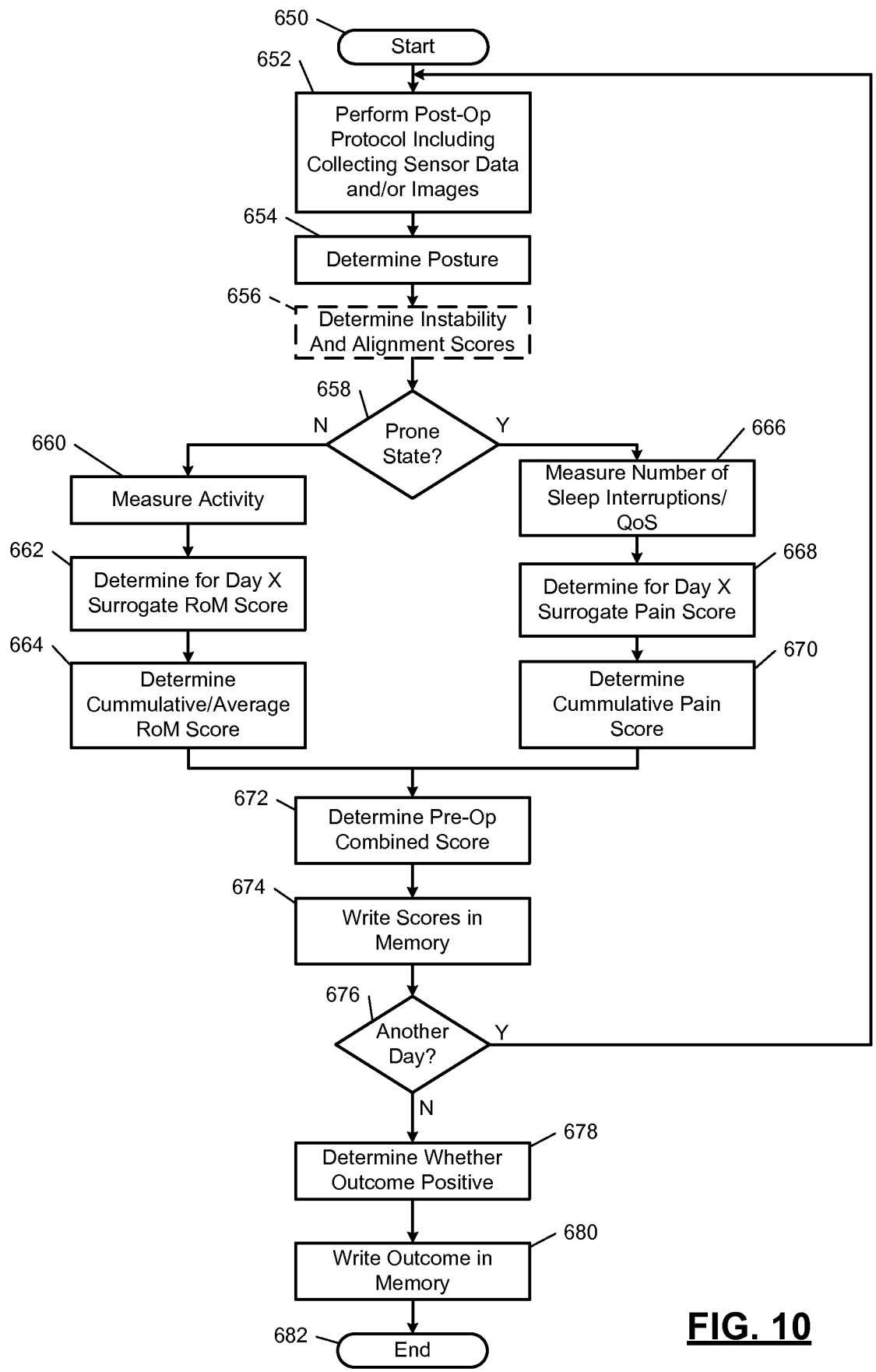
FIG. 10 illustrates a post-operation (Post-Op) method in accordance with the present disclosure.

For further defined structure of the modules of FIGS. 1-6 and 8 see below provided methods of FIGS. 9-10 and below provided definition for the term "module". The systems, devices and modules disclosed herein may be operated using numerous methods, in addition to the methods described above, some additional example methods are illustrated in FIGS. 9-10. In FIG. 9, a Pre-Op method is shown. Although the following tasks are primarily described with respect to the implementations of FIGS. 1-6 and 8, the tasks may be easily modified to apply to other implementations of the present disclosure. The tasks may be iteratively performed.

The methods may be performed for different levels of complexity, examples of which are referred to below as low, medium, and high complexity operating modes. The low complexity operating mode includes collecting data from a small set of one or more physiological sensors and/or sensing modules (e.g., one or more 3-axis sensors and/or one or more 9-axis sensors) for activity, posture, RoM and pain determinations. The medium complexity operating mode may include a larger set of physiological sensors and/or sensing modules (e.g., one or more 3-axis sensors, one or more 9-axis sensors, one or more respiration sensors, and one or more ECG sensors for heart rate and heart rate variability) for RoM and pain determinations. Outputs of the medium complexity mode sensors may be used for calculating stress scores. The additional sensors used for the medium complexity mode provide increased accuracy in determining the below-described scores. The medium complexity mode may include detecting signals from any of the sensors disclosed herein and determining any of the parameters disclosed herein.

The high complexity operating mode includes collecting data from sensors used during the medium operating mode as well as capturing x-ray images of the patient, which may be used to determine activity, RoM, spinal instability and alignment scores. The sensors and/or sensing modules used during the above-stated low, medium and high complexity modes may include, for examples, the sensors and/or sensing modules of FIGS. 3-6. RoM and pain scores may be determined based on the spinal instability and alignment scores as well as the information collected from the sensors. Spinal instability occurs when a vertebra slips from a normal alignment and can be painful. A spinal instability score may indicate and/or be based on an amount of displacement of a first vertebra relative to one or more adjacent vertebrae. A spinal instability may be a leading indication for spine fusion surgery and for this reason may be weighted heavily when determining the RoM and/or pain scores. Separate or combined scores may be determined for spinal instability and spinal alignment.

The method may begin at 600. At 602, the control module 548 may perform a Pre-Op protocol. This may include collecting sensor data from sensors (e.g., the sensors 152 of FIG. 3). This may also include capturing x-ray images magnetic resonance imaging (MRI) images of the patient, depending on whether the corresponding wireless imaging system is operating in the high complexity operating mode. The images may be, for example, of a spine of the patient.

At 604, the posture module 550 determines a posture of the patient based on (i) signals from the sensors (e.g., the sensors 152) and/or corresponding sensor modules, and/or (ii) the x-ray images. Ortho-imaging via a C-arm or O-arm® and corresponding quantitative data analysis may alternatively or also be performed to determine posture. At 606, the spinal module 553 determines an instability and/or alignment score as described above depending on whether operating in the high complexity mode.

At 608, the prone module 552 determines whether the patient is in a prone (or lying down) state based on the posture determined at 604. If the patient is not in a prone state, the patient is determined to be awake and active state and task 610 is performed. If the patient is in a prone state, the patient is determined to be in a rest or sleep state and task 616 is performed.

At 610, the activity/RoM module 554 determines the activity of the patient based on the information detected by and/or generated by the sensors. An activity score (e.g., 1-10) may be generated as described above. The accelerometers may be used as actigraph devices to monitor rest/activity cycles of the patient. The activity score may be generated based on the rest/activity cycles of the patient. While operating in the low complexity mode, the activity may be based on the outputs of the accelerometers. While operating in the medium or high complexity mode, the activity may be based on the outputs of the accelerometers and the other sensors. This may include measuring and/or determining heart rate, heart rate variability and other parameters.

At 612, activity/RoM module 554 determines a RoM score based on the activity score for a current day (or period of time). An activity score provides a baseline surrogate score for RoM and may be used to determine the RoM score. FIG. 11 shows a table of Pre-Op and Post-Op RoM and Pain scores. The table includes 10 example days of Pre-Op RoM percentages for ranges of RoM scores. Weighted daily average scores are shown. The higher the daily average score, the greater the RoM (or more active) the patient. Light activity refers to the range 0-2.5. Medium activity refers to the range 2.6-5.0. High activity refers to the range 5.1-7.5. Vigorous activity refers to the range 7.6-10.

The activity score and/or the RoM score may be determined based on and/or as a function of information detected by the sensors including ECG ramp-rates, inter heart beat intervals, heart beats per minute, peak heart beats per minute, respiration ramp-rates, inter respiration beat intervals, peak inter respiration beat intervals, etc. As an example, a sum of an activity score, an ECG score and a respiration score may be determined to provide a RoM score. The ECG score may be determined based on and/or as a function of the ECG ramp-rates, inter heart beat intervals, heart beats per minute, and peak heart beats per minute. The respiration score may be determined based on and/or as a function of the respiration ramp-rates, inter respiration beat intervals, and peak inter respiration beat intervals. At 614, the first cumulative module 558 determines a cumulative RoM score. The cumulative RoM score may be a sum of the daily averaged RoM scores, as shown.

At 616, the QoS/pain module 556 may determine a number of sleep interruptions during a sleep period and/or a QoS score. The accelerometers may be used as actigraph devices to monitor rest/activity cycles and determine an amount of sleep interruptions. A cross-correlation between acceleration and velocity is an indicator of spinal related pain. While operating in the low complexity mode, the number of sleep interruptions and/or the QoS score may be based on the outputs of the accelerometers. While operating in the medium or high complexity mode, the number of sleep interruptions and/or a QoS score may be based on the outputs of the accelerometers and the other sensors. This may include measuring and/or determining heart rate, heart rate variability and other parameters. The QoS score provides a baseline surrogate score for pain. A low number of interruptions are shown by the range 0-2.5. A medium number of interruptions are shown by the range 2.6-5. A high number of interruptions are shown by the range 5.1-7.5. A very high number of interruptions are shown by the range 7.6-10. Each of the range values may refer to a number of interruptions per sleep period.

At 618, the QoS/pain module 556 determines a pain score (e.g., 1-10). FIG. 11 shows 10 days of Pre-Op pain/QoS percentages. Weighted daily average scores for QoS/pain are shown. The higher the daily average score, the less pain (or better QoS) exhibited by the patient. A stress score and/or pain score may be determined based on and/or as a function of information detected by the sensors including number of sleep interruptions, an ECG heart rate variability value, respiration ramp-rates, inter respiration beat intervals, and peak inter respiration beat intervals. The stress score may more of a neurological score, whereas the pain score may more of a physiological score. The ECG heart rate variability value indicates how much a heart rate changes over a predetermined period of time. As an example, the stress score may be determined based on a sum of the number of sleep interruptions, the ECG heart rate variability value, and the respiration score.

At 620, the second cumulative module 560 determines a cumulative stress and/or pain score is determined based on the weighted daily averages and/or stress scores determined at 618. This may include summing the weighted daily averages of pain/QoS scores, as shown.

At 622, the combined overall module 562 determines a Pre-Op combined score based on the cumulative scores determined at 614, 620. An activity score plus a QoS score provides a combined baseline surrogate score for a sum of a RoM score and a pain score. The Pre-Op combined score may be a sum of the cumulative scores, as shown in FIG. 11. The combined score may also be based on instability and/or alignment scores as determined at 606.

At 624, the control module 548 may store any and/or all of the above-stated scores in one of the memories 304, 348, 354 and/or transmit the scores to server 168. These scores may be stored with other scores for other patients for a particular procedure. The instability and/or alignment scores may be stored separate from and/or in a different memory than the activity, RoM, QoS, pain, and/or cumulative scores.

At 626, the control module 206 may determine whether scores for another day or predetermined period are to be generated. If more scores are to be generated, task 602 may be performed; otherwise task 628 may be performed. The Pre-Op monitoring described above may be conducted for a predetermined period of time (e.g., 1 week) and may be monitored during most activities of daily life of the patient.

At 628, the control module predicts a likelihood (or probability) of a positive outcome for a procedure based on similar Pre-Op (or pre-procedure) scores and corresponding outcome scores. The Pre-Op scores and corresponding outcome scores may be stored in the server 168 and/or in one or more of the memories 304, 348, 354. The server and the memories may store cut-points (or thresholds) for determining whether to perform the procedure. Differences between the above-determined scores and other Pre-Op scores may be determined. If the differences are within predetermined ranges of and/or exceed the corresponding cut-points, and the corresponding outcome scores are positive and/or there is a high probability of a positive outcome, then performance of the procedure may be recommended. The cut-points may be set based on probabilities that a positive outcome will result. For example, if a first cut-point is passed, then a first probability of a positive outcome may be reported. If a second cut-point is passed, then a second probability of a positive outcome may be reported. The cut-points are different. Any number of cut-points may be set and have corresponding probabilities of a positive outcome. The probabilities may be reported (e.g., displayed) via the control module 206 and a corresponding display.

Ortho-imaging via a C-arm or O-arm and corresponding quantitative data analysis may alternatively or also be performed to evaluate spinal mobility for determining a probability of a positive outcome of a surgery. In one embodiment, the combined score, generated based on the cumulative scores, is compared to other Pre-Op scores. In another embodiment, the combined score, generated based on the cumulative scores and the instability and alignment scores, is compared to other Pre-Op scores. In yet another embodiment, differences between one or both of stated the combined scores and other Pre-Op scores are determined. In still another embodiment, differences between the instability and alignment scores and other instability and alignment scores are determined. If the differences (for the combined score and/or the instability and alignment scores) are within predetermined ranges of and/or exceed corresponding cut-points, and the corresponding outcome scores are positive and/or there is a high probability of a positive outcome, then performance of the procedure may be recommended. The above-stated tasks thus include collecting data as a result of physiologic parameter monitoring and medical imaging and based on corresponding cut-points determining a probability that execution of a procedure will provide a positive outcome.

Task 628 may include determining if a surgery or procedure is best choice for a positive outcome. As an example, a current score for a current day may be indicative that surgery or procedure is not required and/or has a low probability of success. However, over time and continuous monitoring a patient with a spinal or degenerative disease may reveal that the scores have worsened and surgery would be recommended. The continuous monitoring and score determinations may be used to determine a best recommended time to perform the surgery to provide a highest probability of success (i.e. highest probability that a positive outcome will result from performing the surgery).

The algorithm used to predict a likelihood of a positive (or negative) outcome may be considered a learning algorithm, as additional data is collected the ability to accurately predict an outcome improves.

At 630, the control module performs task 632 if a negative outcome is predicted. Task 634 is performed if a positive outcome is predicted. At 632, the procedure may be adjusted or cancelled depending on the Pre-Op combined score and/or the differences determined and/or comparisons performed at 628.

At 634, the control module may indicate that the procedure should be performed. The method may end at 636 subsequent performing one of the tasks 632, 634.

FIG. 10 illustrates a Post-Op method in accordance with the present disclosure. The method of FIG. 10 is performed subsequent to performing the method of FIG. 9 and a corresponding procedure. The method of FIG. 10 may be performed a predetermined time period after performing the procedure as a follow up check on results of the procedure. For example, the method of FIG. 10 may be performed 30 days, 60 days and/or 90 days after performing the procedure.

The method may begin at 650. At 652, the control module 548 may perform a Post-Op protocol. This may include collecting sensor data from sensors (e.g., the sensors 152 of FIG. 3). This may also include capturing x-ray images magnetic resonance imaging (MRI) images of the patient, depending on whether the corresponding wireless imaging system is operating in the high complexity operating mode. The images may be, for example, of the spine of the patient.

At 654, the posture module 550 determines a posture of the patient based on (i) signals from the sensors (e.g., the sensors 152) and/or corresponding sensor modules, and/or (ii) the x-ray images. Ortho-imaging via a C-arm or O-arm® and corresponding quantitative data analysis may alternatively or also be performed to determine posture. At 656, the spinal module 553 may determine an instability and/or alignment score as described above depending on whether operating in the high complexity mode.

At 658, the prone module 552 determines whether the patient is in a prone (or lying down) state based on the posture determined at 654. If the patient is not in a prone state, the patient is determined to be awake and active state and task 660 is performed. If the patient is in a prone state, the patient is determined to be in a rest or sleep state and task 666 is performed.

At 660, the activity/RoM module 554 determines the activity of the patient based on the information detected by and/or generated by the sensors. An activity score (e.g., 1-10) may be generated as described above. The accelerometers may be used as actigraph devices to monitor rest/activity cycles of the patient. The activity score may be generated based on the rest/activity cycles of the patient. While operating in the low complexity mode, the activity may be based on the outputs of the accelerometers. While operating in the medium or high complexity mode, the activity may be based on the outputs of the accelerometers and the other sensors. This may include measuring and/or determining heart rate, heart rate variability and other parameters.

At 662, activity/RoM module 554 determines a RoM score based on the activity score for a current day (or period of time). An activity score provides a baseline surrogate score for RoM and may be used to determine the RoM score. The table shown in FIG. 11 includes 10 example days of Post-Op RoM percentages for ranges of RoM scores. Weighted daily average scores are shown. Light activity refers to the range 0-2.5. Medium activity refers to the range 2.6-5.0. High activity refers to the range 5.1-7.5. Vigorous activity refers to the range 7.6-10.

The activity score and/or the RoM score may be determined based on and/or as a function of information detected by the sensors including ECG ramp-rates, inter heart beat intervals, heart beats per minute, peak heart beats per minute, respiration ramp-rates, inter respiration beat intervals, peak inter respiration beat intervals, etc. As an example, a sum of an activity score, an ECG score and a respiration score may be determined to provide a RoM score. The ECG score may be determined based on and/or as a function of the ECG ramp-rates, inter heart beat intervals, heart beats per minute, and peak heart beats per minute. The respiration score may be determined based on and/or as a function of the respiration ramp-rates, inter respiration beat intervals, and peak inter respiration beat intervals. At 664, the first cumulative module 558 determines a cumulative RoM score. The cumulative RoM score may be a sum of the daily averaged RoM scores, as shown.

At 666, the QoS/pain module 556 may determine a number of sleep interruptions during a sleep period and/or a QoS score. The accelerometers may be used as actigraph devices to monitor rest/activity cycles and determine an amount of sleep interruptions. A cross-correlation between acceleration and velocity is an indicator of spinal related pain. While operating in the low complexity mode, the number of sleep interruptions and/or the QoS score may be based on the outputs of the accelerometers. While operating in the medium or high complexity mode, the number of sleep interruptions and/or a QoS score may be based on the outputs of the accelerometers and the other sensors. This may include measuring and/or determining heart rate, heart rate variability and other parameters. The QoS score provides a baseline surrogate score for pain. A low number of interruptions are shown by the range 0-2.5. A medium number of interruptions are shown by the range 2.6-5. A high number of interruptions are shown by the range 5.1-7.5. A very high number of interruptions are shown by the range 7.6-10. Each of the range values may refer to a number of interruptions per sleep period.

At 668, the QoS/pain module 556 determines a pain score (e.g., 1-10). FIG. 11 shows 10 days of Post-Op pain/QoS percentages. Weighted daily average scores for QoS/pain are shown. A stress score and/or pain score may be determined based on and/or as a function of information detected by the sensors including number of sleep interruptions, an ECG heart rate variability value, respiration ramp-rates, inter respiration beat intervals, and peak inter respiration beat intervals. The stress score may more of a neurological score, whereas the pain score may more of a physiological score. The ECG heart rate variability value indicates how much a heart rate changes over a predetermined period of time. As an example, the stress score may be determined based on a sum of the number of sleep interruptions, the ECG heart rate variability value, and the respiration score.

At 670, the second cumulative module 560 determines a cumulative stress and/or pain score is determined based on the weighted daily averages and/or stress scores determined at 618. This may include summing the weighted daily averages of pain/QoS scores, as shown.

At 672, the combined overall module 562 determines a Post-Op combined score based on the cumulative scores determined at 664, 670. An activity score plus a QoS score provides a combined baseline surrogate score for a sum of a RoM score and a pain score. The Post-Op combined score may be a sum of the cumulative scores, as shown in FIG. 11. The Post-Op combined score may also be based on instability and/or alignment scores as determined at 656.

At 674, the control module 548 may store any and/or all of the above-stated scores in one of the memories 304, 348, 354 and/or transmit the scores to server 168. These scores may be stored with other scores for other patients for a particular procedure. The instability and/or alignment scores may be stored separate from and/or in a different memory than the activity, RoM, QoS, pain, and/or cumulative scores.

At 676, the control module 206 may determine whether scores for another day or predetermined period are to be generated. If more scores are to be generated, task 652 may be performed; otherwise task 678 may be performed. The Post-Op monitoring described above may be conducted for a predetermined period of time (e.g., 1 week) and may be monitored during most activities of daily life of the patient.

At 678, the control module determines an outcome score indicative of whether an outcome of the procedure is positive. A sum of a Post-Op activity score and a corresponding Post-Op QoS score minus a sum of the Pre-Op activity score and the corresponding Pre-Op QoS score provides an outcome score that is indicative of whether the outcome of the procedure performed is positive. A sum of a Post-Op RoM score and a corresponding Post-Op pain score minus a sum of the Pre-Op RoM score and the corresponding Pre-Op pain score provides an outcome score that is indicative of whether the outcome of the procedure performed is positive. The differences may be determined based on a day-by-day basis or for a more accurate outcome determination may be determined based on a difference between cumulative scores for a predetermined period of time (e.g., 1 week). For example, a sum of the Post-Op cumulative activity score and the corresponding Post-Op cumulative QoS score minus a sum of the Pre-Op cumulative activity score and the corresponding Pre-Op cumulative QoS score provides an outcome score that is indicative of whether the outcome of the procedure performed is positive. A sum of the Post-Op cumulative RoM score and the corresponding Post-Op cumulative pain score minus a sum of the Pre-Op cumulative RoM score and the corresponding Pre-Op cumulative pain score provides an outcome score that is indicative of whether the outcome of the procedure performed is positive.

If one or more of the differences determined are positive, then the outcome of the procedure is positive. Similarly, if one or more of the differences determined are negative, then the outcome of the procedure is negative.

At 680, the outcome scores, the differences, and/or whether the outcome is positive or negative maybe stored in one of the memories 304, 348, 354 for the procedure performed. This information may then be referenced for future probability of positive outcome determinations. The method may end at 682.

The above-described tasks of FIGS. 9-10 are meant to be illustrative examples; the tasks may be performed sequentially, synchronously, simultaneously, continuously, during overlapping time periods or in a different order depending upon the application. Also, any of the tasks may not be performed or skipped depending on the implementation and/or sequence of events.

As stated above, respiration rates may be monitored. In addition to respiration rates, blood oxygen levels may also be monitored to detect sleep apnea. This may be helpful in distinguishing sleep interruption due to pain from sleep apnea.

Also, to detect patient activity, movement of a patient may be detected via optical sensors and/or accelerometers. For example, optical analysis and optical diagnosis may be performed to detect movement and activity of a patient. Markers may be placed at key points on the anatomy of a patient. For example, markers may be placed on an iliac crest, spine, knees, shoulders, and/or other parts of a patient and movement of the markers may be detected via optical sensors. Thus, the above-disclosed systems may include optical sensors for monitoring, tracking and detecting position and movement of markers and/or other objects. Signals from the optical sensors may be received by one or more of the above-disclosed modules. Accelerometers located on a patient may detect the force of heal strikes as a patient walks or runs. The signals from the accelerometers may be used for gait analysis to augment the optical monitoring. This may also be performed by one or more of the above-disclosed modules.

In addition, the disclosed sensing modules may include and/or be connected to force sensing elements. The force sensing elements may include strain gauges, piezo-electric or piezo-resistive elements, and/or other force sensing elements. The sensing elements may be non-intrusive elements and generate signals received by control modules (e.g., the control module 206 of FIG. 6) of the sensing modules. The other sensing elements 417 may include the force sensing elements. The force sensing elements may be used to detect compression force (e.g., hand compression force) and/or push or pull forces (e.g., arm push or pull force). The force sensing elements may be utilized, for example, during the medium complexity operating mode and/or the high complexity operating mode in order to determine strength quantification values indicative of strength of a patient (e.g., upper body strength). Loss of upper body strength is an indicator of spine health. In one embodiment, a strength determination is not performed during the low complexity operating mode, a hand compression force (e.g., determined by squeezing a rubber ball having a force-gauge or force sensing element) is determined during the medium complexity operating mode, and a hand compression force and an arm push and/or pull force are determined during the high complexity operating mode. The force determinations and strength values may be used in the methods disclosed herein to the range of motion values and/or quality of sleep values.

The above disclosed examples provide systems for providing clinical evidence for positive procedure outcomes. The systems determine pre and post scores for determining times for maximizing probability of positive outcomes and for determining whether a procedure has provided a positive outcome. The probabilities are determined based on stored historical data that continues to grow with each additionally performed procedure.

The wireless communications described in the present disclosure can be conducted in full or partial compliance with IEEE standard 802.11-2012, IEEE standard 802.16-2009, IEEE standard 802.20-2008, and/or Bluetooth Core Specification v4.0. In various implementations, Bluetooth Core Specification v4.0 may be modified by one or more of Bluetooth Core Specification Addendums 2, 3, or 4. In various implementations, IEEE 802.11-2012 may be supplemented by draft IEEE standard 802.11ac, draft IEEE standard 802.11ad, and/or draft IEEE standard 802.11ah.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The apparatuses and methods may be implemented in, for example, a handheld instrument, a tablet, a smart phone, a cellular phone, and/or other computing device. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

What is claimed is:

1. A spinal kinematics system for measuring objective parameters used to determine whether an outcome of a procedure is positive based on vertebral motion analysis of a patient, the system comprising:
   at least one imaging sensor configured to image and measure vertebral displacement;
   at least one motion sensor configured detect motion of a patient; and
   a monitoring device that comprises:
      a wireless interface adapter in communication with and which receives information from the at least one imaging sensor and the at least one motion sensor, and
      a control circuit having a processor and a memory and is configured to process information received from the at least one imaging sensor and the at least one motion sensor;
   wherein the control circuit is further configured to determine, post-operation for the patient:
      an activity score, based on the vertebral displacement measured by the at least one imaging sensor and the motion detected by the at least one motion sensor, that measures a rest-activity cycle of the patient for a predetermined activity period;
      a cumulative activity score by summing weighted daily averages of a plurality of activity scores across a plurality of predetermined activity periods;
      a combined score calculated using the cumulative activity score; and
      whether the outcome of the procedure is positive by comparing the combined score to a second combined score, the second combined score being determined for the patient prior to performing the procedure.

2. The system according to claim 1, wherein the at least one motion sensor is a three-axis motion sensor or nine-axis motion sensor.

3. The system according to claim 1, wherein the activity score is further determined by measuring a size of a radius of an arc formed by a curvature of a spine of the patient.

4. The system according to claim 1, wherein the activity score is determined based on a scale of 0 to 10.

5. The system according to claim 1, further comprising:
   at least one parametric sensor configured to measure one or more first parameters associated with the patient,
   wherein the control circuit is further configured to determine a quality of sleep score, based on information generated by the at least one parametric sensor, the at least one parametric sensor being further configured to measure a number of sleep interruptions during a predetermined sleep period.

6. The system according to claim 5, wherein one or more first parameters are selected from a list consisting of voltages, frequencies, current levels, durations, amplitudes, temperatures, impedances, resistances, and wavelengths.

7. The system according to claim 5, wherein the activity score is further based on one or more second parameters generated by the monitoring device using one or more of the first parameters generated by the at least one parametric sensor.

8. The system according to claim 7, wherein the one or more second parameters are selected from a list consisting of durations, oxygen levels, temperatures, impedances, pH levels, accelerations, amplitudes, heart rates, blood pressures, electro-cardiogram (ECG) parameters, respiratory parameters, body activity values, heart sounds, blood gas pH, red blood cell counts, white blood cell counts, and electro-encephologram (EEG) parameters.

9. The system according to claim 5, wherein the control circuit further comprises a posture circuit configured to analyze information generated by the at least one imaging sensor and the at least one motion sensor, wherein the control circuit is further configured to determine:
 a posture state of the patient, using the posture circuit, based on information generated by the at least one imaging sensor and the at least one motion sensor;
 a motion score based on information generated by the at least one motion sensor; and
 a pain score based on the number of sleep interruptions, wherein the activity score of the patient is further determined based on the posture state of the patient and the activity score; and
 wherein the quality of sleep score of the patient is further determined based on the posture state of the patient and the pain score.

10. The system according to claim 9, wherein the control circuit further comprises a prone circuit configured to analyze information generated by the at least one imaging sensor and the at least one motion sensor, and wherein the control circuit is further configured to determine:
 whether the patient is in a prone state using the prone circuit;
 the quality of sleep score if the patient is in the prone state; and
 the activity score if the patient is not in the prone state.

11. A method for measuring, post-operation for a patient, objective parameters used to determine whether an outcome of a procedure is positive based on vertebral motion analysis of the patient for use in a spinal kinematics system, the method comprising:
 measuring, using at least one imaging sensor, vertebral displacement;
 detecting, using at least one motion sensor, motion of the patient;
 calculating, based on the measured vertebral displacement and the detected motion, an activity score that measures a rest-activity cycle of the patient for a predetermined activity period;
 determining a cumulative activity score based on weighted daily averages of a plurality of activity scores across a plurality of predetermined activity periods;
 determining a combined score calculated using at least the cumulative activity score; and determining whether the outcome of the procedure is positive by comparing the combined score to a second combined score, the second combined score being determined for the patient prior to performing the procedure.

12. The method according to claim 11, wherein the at least one motion sensor is a three-axis motion sensor or nine-axis motion sensor.

13. The method according to claim 11, further comprising measuring a spinal curvature of the patient based on a size of a radius of an arc formed by a curvature of a spine, wherein the activity score is determined using the spinal curvature.

14. The method according to claim 11, wherein the activity score is determined based on a scale of 0 to 10.

15. The method according to claim 11, further comprising:
 measuring, using at least one parametric sensor, one or more first parameters associated with the patient;
 calculating, based on the detected motion and one or more of the first parameters, a quality of sleep score that measures a number of sleep interruptions during a predetermined sleep period;
 determining a cumulative quality of sleep score based on weighted daily averages of a plurality of quality of sleep scores across a plurality of predetermined sleep periods; and
 determining the combined baseline score by calculating the sum of the cumulative activity score and the cumulative quality of sleep score.

16. The method according to claim 15, wherein the first parameters are selected from a list consisting of voltages, frequencies, current levels, durations, amplitudes, temperatures, impedances, resistances, and wavelengths.

17. The method according to claim 15, further comprising generating, based on the one or more first parameters, one or more second parameters, wherein the activity score is further based on the one or more second parameters.

18. The method according to claim 17, wherein the one or more second parameters are selected from a list consisting of durations, oxygen levels, temperatures, impedances, pH levels, accelerations, amplitudes, heart rates, blood pressures, electro-cardiogram (ECG) parameters, respiratory parameters, body activity values, heart sounds, blood gas pH, red blood cell counts, white blood cell counts, and electro-encephologram (EEG) parameters.

19. The method of claim 15, further comprising:
 determining, using a posture circuit, a posture state of the patient based on information generated by the at least one imaging sensor and the at least one motion sensor;
 determining a motion score based the motion detected by the at least one motion sensor;
 determining a pain score based on the number of sleep interruptions;
 determining the activity score based on the posture state of the patient and the activity score; and
 determining the quality of sleep score of the patient based on the posture state of the patient and the pain score.

20. The method according to claim 19, further comprising:
 determining, using a prone circuit, whether the patient is in a prone state based on information generated by the at least one imaging sensor and the at least one motion sensor;
 determining the quality of sleep score if the patient is in the prone state; and determining the activity score if the patient is not in the prone state.

21. The method according to claim 11, further comprising predicting an outcome of a second procedure based on the determined outcome and the combined score.

\* \* \* \* \*